United States Patent [19]

Setoi et al.

[11] Patent Number: 5,514,701

[45] Date of Patent: May 7, 1996

[54] PYRROLIDINE DERIVATIVES

[75] Inventors: Hiroyuki Setoi; Akihiko Sawada; Hirokazu Tanaka; Masashi Hashimoto, all of Tsukuba, Japan

[73] Assignee: Fujisawa Pharmaceutical Co., Ltd., Osaka, Japan

[21] Appl. No.: 95,350

[22] Filed: Jul. 23, 1993

Related U.S. Application Data

[62] Division of Ser. No. 843,196, Feb. 28, 1992, Pat. No. 5,264,453, which is a division of Ser. No. 421,399, Oct. 13, 1989, Pat. No. 5,130,323.

[30] Foreign Application Priority Data

Oct. 31, 1988 [GB] United Kingdom ............... 8825454
Apr. 13, 1989 [GB] United Kingdom ............... 8908387

[51] Int. Cl.⁶ ................. C07D 207/14; A61K 31/40
[52] U.S. Cl. ................. 514/422; 514/826; 548/517; 548/524; 548/527
[58] Field of Search ................. 514/422, 826; 548/527, 524, 517

[56] References Cited

U.S. PATENT DOCUMENTS

| | | |
|---|---|---|
| 4,210,660 | 7/1980 | Takashima et al. . |
| 4,785,119 | 11/1988 | Hojo et al. . |
| 4,916,152 | 4/1990 | Setoi et al. . |
| 5,130,323 | 7/1992 | Setoi et al. . |

FOREIGN PATENT DOCUMENTS

| | | |
|---|---|---|
| 0289911 | 11/1988 | European Pat. Off. . |
| 61-257966 | 11/1986 | Japan . |
| 63-51370 | 3/1988 | Japan . |

OTHER PUBLICATIONS

Frans M. Kaspersen et al: J. C. S. Perkin I 1975, pp. 1617–1622.

Frans M. Kaspersen et al: J. C. S. Perkin I 1975, pp. 1798–1802.

Patrick E. Hanna et al: Journal of Medical Chemistry, 1973, vol. 16, No. 9, pp. 963–967.

A. M. Sepulchre et al: Carbohyd. Res., 14 (1970) 1–8.

A. M. Sepulchre et al: C. R. Acad. Sc. Paris, t. 268 (3 mars 1969), pp. 849–851.

Frans M. Kaspersen et al: Heterocycles 2 (1974), pp. 15–19.

*Primary Examiner*—Shean C. Wu
*Assistant Examiner*—Catherine Kilby Scalzo
*Attorney, Agent, or Firm*—Oblon, Spivak, McClelland, Maier & Neustadt

[57] ABSTRACT

This invention relates to pyrrolidine derivatives and pharmaceutically acceptable salts, their pharmaceutical compositions, and methods of use as thromboxane $A_2$ antagonists and/or thromboxane $A_2$ synthetase inhibitors in the treatment of thrombotic diseases, asthma or nephritis, e.g. of the formula:

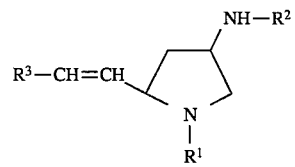

wherein $R^1$ is thienyl(lower)alkyl, furyl(lower)alkyl or pyrrolyl(lower)alkyl.

5 Claims, No Drawings

PYRROLIDINE DERIVATIVES

This is a division of application Ser. No. 07/843,196, filed on Feb. 28, 1992, now U.S. Pat. No. 5,264,453 which is a DIV of Ser. No. 07/421,399, filed on Oct. 13, 1989 now U.S. Pat. No. 5,130,323.

This invention relates to new pyrrolidine derivatives and pharmaceutically acceptable salts thereof.

More particularly, it relates to new pyrrolidine derivatives and pharmaceutically acceptable salts thereof which have thromboxane $A_2$ ($TXA_2$) antagonism and $TXA_2$ synthetase-inhibitory activity and can be used for treating and/or preventing thrombotic diseases such as transient cerebral ischemic attack, cerebral apoplexy, unstable angina, myocardial infarction, peripheral circulatory insufficiency, thrombus formation after percutaneous transluminal coronary angioplasty, disseminated intravascular coagulation syndrome or the like; allergic diseases such as asthma or the like; nephritis; peptic ulcer; hemicrania; diabetic neuropathy; diabetic angiopathy; restenosis after percutaneous transluminal coronary angioplasty; adult respiratory distress syndrome; shock; hepatitis; cerebral vasospasm after subarachnoidal hemorrhage; hypertension; arteriosclerosis; cancerous metastasis, thrombus formation on extracorporeal circulation; thrombus formation on transplantation; and the like and for reducing nephrotoxicity induced by immunosuppressants such as ciclosporin at renal transplantation, and can be also used with fibrinolytic agents in order to increase the effect of fibrinolytic agents.

The pyrrolidine derivatives of this invention can be represented by the following formula (I):

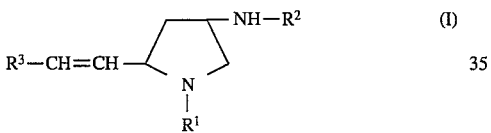

wherein
$R^1$ is alkyl, ar(lower)alkyl which may have suitable substituent(s), or heterocyclic(lower)alkyl,
$R^2$ is hydrogen or an acyl group, and
$R^3$ is carboxy(lower)alkyl, protected carboxy(lower)alkyl, carboxyaryl or protected carboxyaryl.

According to the present invention, the new pyrrolidine derivatives (I) can be prepared by the processes which are illustrated in the following scheme.

Process 1

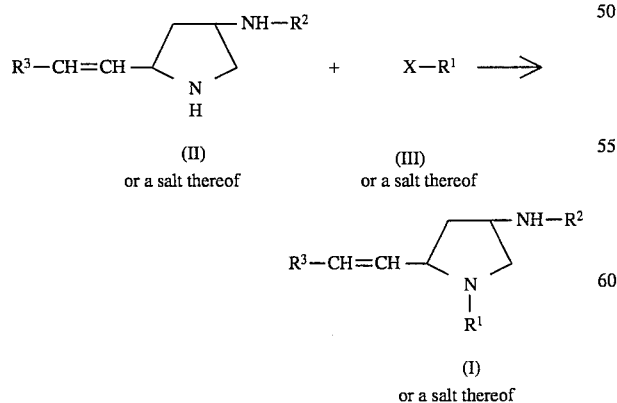

Process 2

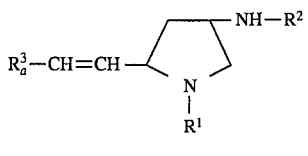

(Ia)
or a salt thereof

↓ Elimination reaction of the carboxy protective group

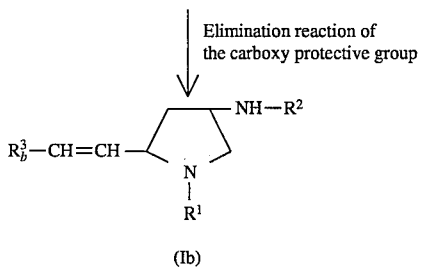

(Ib)
or a salt thereof

Process 3

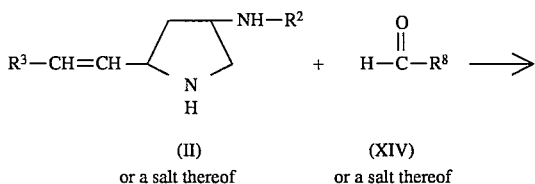

(II)                (XIV)
or a salt thereof    or a salt thereof

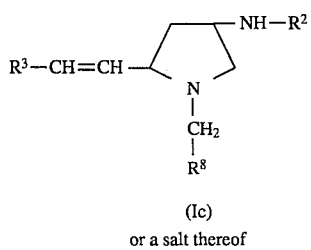

(Ic)
or a salt thereof

Process 4

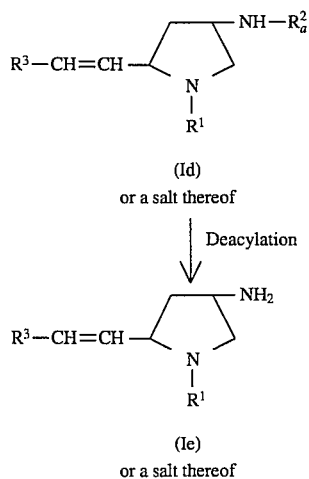

(Id)
or a salt thereof

↓ Deacylation (Ie)
or a salt thereof

Process 5

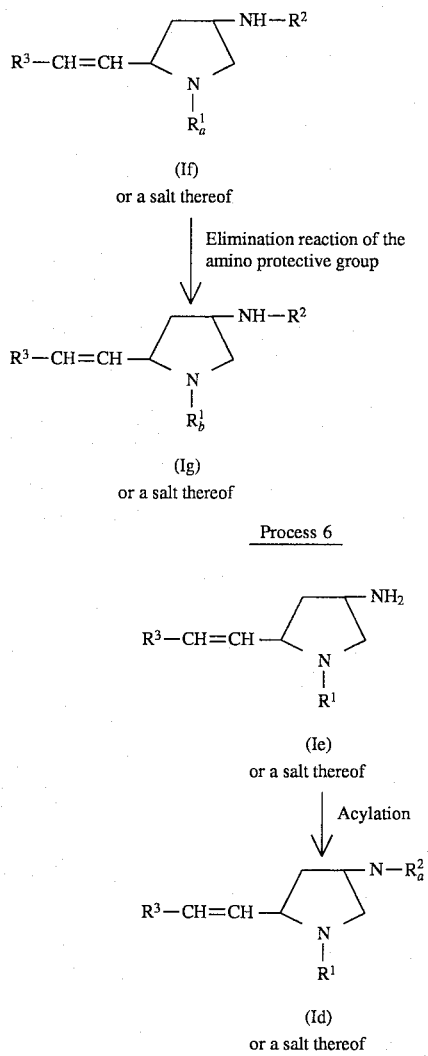

wherein
R¹, R² and R³ are each as defined above
X is halogen,
$R_a^3$ is protected carboxy(lower)alkyl or protected carboxyaryl,
$R_b^3$ is carboxy(lower)alkyl or carboxyaryl,
$R^8$ is hydrogen, $(C_1-C_{14})$alkyl, aryl which may have suitable substituent(s), ar$(C_1-C_5)$alkyl which may have suitable substituent(s), a heterocyclic group, or heterocyclic $(C_1-C_5)$alkyl,
$R_a^2$ is an acyl group,
$R_a^1$ is ar(lower)alkyl having an amino group, and
$R_b^1$ is ar(lower)alkyl having an amino group.

The starting compound (II) can be prepared by the following processes.

Process A

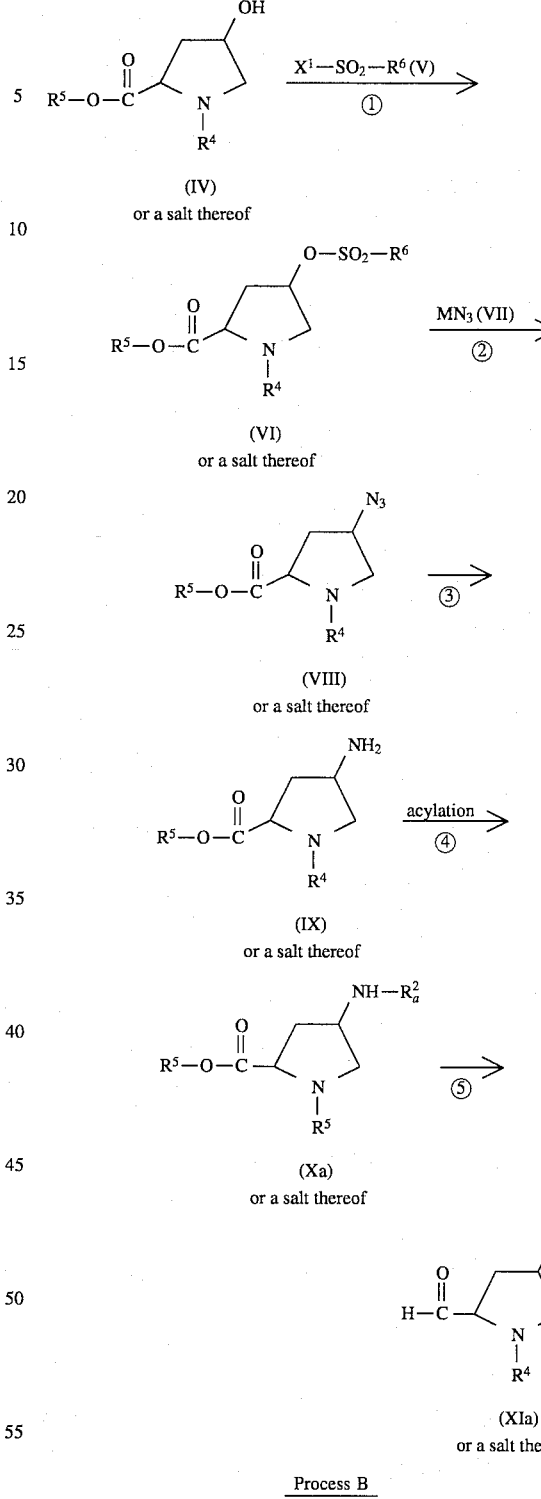

Process B

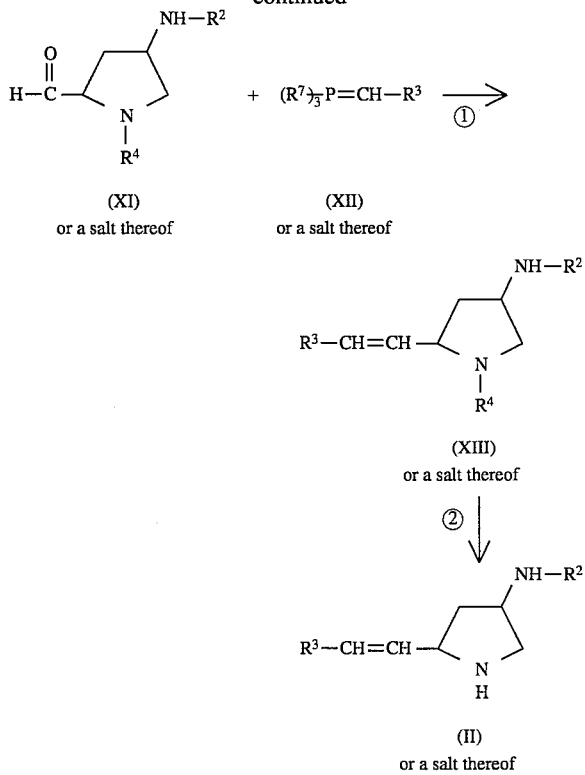

wherein
R², R_a² and R³ are each as defined above,
R⁴ is an imino protective group,
R⁵ is lower alkyl,
R⁶ is lower alkyl,
X¹ is halogen,
M is an alkaline metal and
R⁷ is aryl.

In the above and subsequent descriptions of the present specification, suitable examples and illustrations of the various definitions which the present invention include within the scope thereof are explained in detail as follows.

The term "lower" is intended to mean 1 to 6 carbon atom(s), preferably 1 to 4 carbon atom(s), unless otherwise indicated.

Suitable "alkyl" may include straight or branched one having 1 to 15 carbon atom(s), such as methyl, ethyl, propyl, isopropyl, butyl, isobutyl, sec-butyl, t-butyl, pentyl, t-pentyl, hexyl, heptyl, octyl, nonyl, decyl, undecyl, dodecyl, tridecyl, tetradecyl, pentadecyl or the like.

Suitable "lower alkyl" and "lower alkyl moiety" in the terms "heterocyclic(lower)alkyl", "carboxy(lower)alkyl" and "protected carboxy(lower)alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "lower alkyl moiety" in the term "ar(lower)alkyl" may include straight or branched one having 1 to 6 carbon atom(s) as mentioned above, preferably one having 1 to 5 carbon atom(s).

Suitable "aryl" and "aryl moiety" in the terms "ar(lower)alkyl", "carboxyaryl", "protected carboxyaryl" and "ar(C₁–C₅)alkyl" may include phenyl, naphthyl and the like.

Suitable "substituent" in the terms "ar(lower)alkyl which may have suitable substituent(s)", "aryl which may have suitable substituent(s)" and ar(C₁–C₅)alkyl which may have suitable substituent(s)" may include cyano, hydroxy, halogen (e.g. chlorine, bromine, fluorine and iodine), lower alkyl (e.g., methyl, ethyl, propyl, isopropyl, butyl, isobutyl, sec-butyl, t-butyl, pentyl, t-pentyl, hexyl, etc.), lower alkoxy (e.g., methoxy, ethoxy, propoxy, isopropoxy, butoxy, isobutoxy, sec-butoxy, t-butoxy, pentyloxy, t-pentyloxy, hexyloxy, etc.), aryl (e.g., phenyl, naphthyl, etc.), amino, di(lower)alkylamino (e.g. dimethylamino, diethylamino, dipropylamino, dibutylamino, dipentylamino, dihexylamino, etc.), protected amino and the like.

Suitable "protected amino" may include acylamino and the like.

Suitable "(C₁–C₅)alkyl moiety" in the terms "ar(C₁–C₅)alkyl" and "heterocyclic(C₁–C₅)alkyl" may include straight or branched one having 1 to 5 carbon atom(s), such as methyl, ethyl, propyl, isopropyl, butyl, isobutyl, sec-butyl, t-butyl, pentyl, t-pentyl or the like.

Suitable "(C₁–C₁₄)alkyl" may include straight or branched one having 1 to 14 carbon atom(s), such as methyl, ethyl, propyl, isopropyl, butyl, isobutyl, sec-butyl, t-butyl, pentyl, t-pentyl, hexyl, heptyl, octyl, nonyl, decyl, undecyl, dodecyl, tridecyl, tetradecyl or the like.

Suitable "heterocyclic group" and "heterocyclic moiety" in the terms "heterocyclic(lower)alkyl" and "heterocyclic(C₁–C₅)alkyl" means saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidino, piperazinyl, etc.;

unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.;

unsaturated 3 to 8-membered (more preferably 5 or 6 membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing a sulfur atom, for example, thienyl, etc.;

unsaturated 3 to 8-membered (more preferably 5 or 6-membered) heteromonocyclic group containing an oxygen atom, for example, furyl, etc.;

unsaturated condensed heterocyclic group containing 1 to 2 sulfur atom(s) and 1 to 3 nitrogen atom(s), for example, benzothiazolyl, benzothiadiazolyl, etc. and the like.

Suitable "acyl" and "acyl moiety" in the term "acylamino" may include lower alkanoyl (e.g., formyl, acetyl, propionyl, butyryl, isobutyryl, valeryl, isovaleryl, pivaloyl, etc.), lower alkoxycarbonyl (e.g., methoxycarbonyl, ethoxycarbonyl, propoxycarbonyl, isopropoxycarbonyl, butoxycarbonyl, t-butoxycarbonyl, pentyloxycarbonyl, t-pentyloxycarbonyl, hexyloxycarbonyl, etc.), lower alkylsulfonyl (e.g. methylsulfonyl, ethylsulfonyl, propylsulfonyl, isopropylsulfonyl, butylsulfonyl, t-butylsulfonyl, pentylsulfonyl, t-pentylsulfonyl, hexylsulfonyl, etc.), arylsulfonyl (e.g., phenylsulfonyl, naphthylsulfonyl, etc.), aroyl (e.g. benzoyl, naphthoyl, etc.), ar(lower)alkanoyl (e.g., phenylacetyl, phenylpropionyl, etc.), cyclo(lower)alkyl(lower)alkanoyl (e.g. cyclohexylacetyl, cyclopentylacetyl, etc.), ar(lower)alkoxycarbonyl (e.g., benzyloxycarbonyl, phenethyloxycarbonyl, etc.), arylcarbamoyl (e.g., phenylcarbamoyl, naphthylcarbamoyl, etc.), heterocyclicsulfonyl such as heteromonocyclicsulfonyl (e.g., thienylsulfonyl, furylsulfonyl, pyridylsulfonyl, etc.) and the like; and said acyl groups may be substituted with 1 to 3 suitable substituent(s) such as halogen (e.g., chlorine, bromine, fluorine and iodine), lower alkyl (e.g., methyl, ethyl, propyl, isopropyl, butyl, isobutyl, sec-butyl, t-butyl, pentyl, t-pentyl, hexyl, etc.), lower alkoxy (e.g. methoxy, ethoxy, propoxy, isopropoxy, butoxy, t-butoxy, pentyloxy, t-pentyloxy, hexyloxy, etc.), nitro, mono (or di or tri)halo(lower)alkyl (e.g. chloromethyl, bromomethyl, chloropropyl, 1,2-dichloroethyl, 1,2-dibromoethyl, 2,2-dichloroethyl, trifluoromethyl, 1,2,2-trichloroethyl, etc.) or the like.

Suitable "protected carboxy moiety" in the terms "protected carboxy(lower)alkyl" and "protected carboxyaryl" may include carbamoyl; acylcarbamoyl such as lower alkylsulfonylcarbamoyl (e.g., methylsulfonylcarbamoyl, ethylsulfonylcarbamoyl, propylsulfonylcarbamoyl, isopropylsulfonylcarbamoyl, butylsulfonylcarbamoyl, t-butylsulfonylcarbamoyl, pentylsulfonylcarbamoyl, t-pentylsulfonylcarbamoyl, hexylsulfonylcarbamoyl, etc.), arylsulfonylcarbamoyl (e.g., phenylsulfonylcarbamoyl, naphthylsulfonylcarbamoyl, etc.) or the like; esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.), lower alkenyl ester (e.g., vinyl ester, allyl ester, etc.), lower alkynyl ester (e.g. ethynyl ester, propynyl ester, etc.), mono(or di or tri)-halo(lower)alkyl ester (e.g., 2-iodoethyl ester, 2,2,2-trichloroethyl ester, etc.), lower alkanoyloxy(lower)alkyl ester (e.g., acetoxymethyl ester, propionyloxymethyl ester, 1-acetoxypropyl ester, valeryloxymethyl ester, pivaloyloxymethyl ester, hexanoyloxymethyl ester, 1-acetoxyethyl ester, 2-propionyloxyethyl ester, 1-isobutyryloxyethyl ester, etc.), lower alkanesulfonyl(lower)alkyl ester (e.g., mesylmethyl ester, 2-mesylethyl ester, etc.), ar(lower)alkyl ester, for example, phenyl(lower)alkyl ester which may be substituted with one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiary butylbenzyl ester, etc.), lower alkoxycarbonyloxy(lower)alkyl ester (e.g., methoxycarbonyloxymethyl ester, ethoxycarbonyloxymethyl ester, ethoxycarbonyloxyethyl ester, etc.), aroyloxy(lower)alkyl ester (e.g., benzoyloxymethyl ester, benzoyloxyethyl ester, toluoyloxyethyl ester, etc.), aryl ester which may have one or more suitable substituent(s) (e.g., phenyl ester, tolyl ester, tertiarybutylphenyl ester, xylyl ester, mesityl ester, cumenyl ester, etc.); and the like.

Suitable "halogen" may include chlorine, bromine, fluorine and iodine.

Suitable "imino protective group" may include an acyl group as mentioned above and the like.

Suitable "alkaline metal" may include sodium, potassium and the like.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, lysine, etc.), and the like.

Preferred embodiments of the object compound (I) are as follows.

$R^1$ is unsaturated 5 or 6-membered heteromonocyclic(lower)alkyl in which heteromonocyclic group contains 1 to 4 nitrogen atom(s) [more preferably pyridyl(lower)alkyl, pyrazinyl(lower)alkyl, pyrrolyl(lower)alkyl or imidazolyl(lower)alkyl, most preferably pyridyl($C_1$–$C_4$)alkyl, pyrazinyl($C_1$–$C_4$)alkyl, pyrrolyl($C_1$–$C_4$)alkyl or imidazolyl($C_1$–$C_4$)alkyl], unsaturated condensed heterobicyclic-(lower)alkyl in which heterobicyclic group contains 1 to 4 nitrogen atom(s) [more preferably quinolyl(lower)alkyl, most preferably quinolyl($C_1$–$C_4$)alkyl], unsaturated condensed heterobicyclic-(lower)alkyl in which heterobicyclic group contains 1 to 2 oxygen atom(s) and 1 to 3 nitrogen atom(s) [more preferably benzoxazolyl(lower)alkyl, most preferably benzoxazolyl($C_1$–$C_4$)alkyl], unsaturated 5 or 6-membered heteromonocyclic-(lower)alkyl in which heteromonocyclic group contains 1 to 2 sulfur atom(s) and 1 to 3 nitrogen atom(s) [more preferably thiazolyl(lower)alkyl, most preferably thiazolyl($C_1$–$C_4$)alkyl], unsaturated 5 or 6-membered heteromonocyclic-(lower)alkyl in which heteromonocyclic group contains a sulfur atom [more preferably thienyl(lower)alkyl, most preferably thienyl($C_1$–$C_4$)alkyl], unsaturated 5 or 6-membered-heteromonocyclic-(lower)alkyl in which heteromonocyclic group contains an oxygen atom [more preferably furyl(lower)alkyl, most preferably furyl($C_1$–$C_4$)alkyl], unsaturated condensed heterobicyclic-(lower)alkyl in which heterobicyclic group contains 1 to 2 sulfur atom(s) and 1 to 3 nitrogen atom(s) [more preferably benzothiazolyl(lower)alkyl, most preferably benzothiazolyl($C_1$-$C_4$)alkyl], $C_1$-$C_{15}$ alkyl [more preferably $C_1$-$C_{12}$ alkyl], phenyl(lower)alkyl which may have 1 to 3 substituent(s) selected from the group consisting of cyano, hydroxy, halogen, lower alkyl, lower alkoxy, aryl, amino, di(lower)alkylamino and protected amino [more preferably phenyl(lower)alkyl which may have 1 to 2 substituent(s) selected from the group consisting of cyano, hydroxy, halogen, lower alkyl, lower alkoxy, phenyl, amino, di(lower)alkylamino and acylamino, most preferably phenyl(lower)alkyl, cyanophenyl(lower)alkyl, hydroxyphenyl(lower)alkyl, mono (or di)halophenyl(lower)alkyl, lower alkylphenyl(lower)alkyl, lower alkoxyphenyl(lower)alkyl, phenylphenyl(lower)alkyl, diphenyl(lower)alkyl, aminophenyl(lower)alkyl, di(lower alkyl)amino-phenyl(lower)alkyl, or lower alkanoylaminophenyl(lower)alkyl], or naphthyl(lower)alkyl, $R^2$ is hydrogen, ar(lower)alkoxycarbonyl [more preferably phenyl(lower)alkoxycarbonyl], or arylsulfonyl which may have 1 to 3 substituent(s) selected from the group consisting of halogen, lower alkyl, lower alkoxy and mono(or di or tri)halo(lower)alkyl [more preferably phenylsulfonyl which may have 1 to 2 substituent(s) selected from the group consisting of halogen, lower alkyl, lower alkoxy and mono(or di or tri)halo(lower)alkyl, most preferably phenylsulfonyl which may have halogen, lower alkyl, lower alkoxy or mono(or di or tri)halo-lower alkyl], $R^3$ is carboxy(lower)alkyl, protected carboxy(lower)alkyl [more preferably esterified carboxy(lower)alkyl, most preferably lower alkoxycarbonyl(lower)alkyl], carboxyphenyl or protected carboxyphenyl [more preferably esterified carboxyphenyl, most preferably lower alkoxycarbonylphenyl].

The processes for preparing the object compound (I) and starting compound (II) of the present invention are explained in detail in the following.

Process 1

The compound (I) or a salt thereof can be prepared by reacting the compound (II) or a salt thereof with the compound (III) or a salt thereof.

The reaction is usually carried out in a conventional solvent such as acetone, dioxane, chloroform, methylene chloride, ethylene chloride, tetrahydrofuran, ethyl acetate, N,N-dimethylformamide, dimethyl sulfoxide or any other solvent which does not adversely influence the reaction.

The reaction temperature is not critical and the reaction is usually carried out at room temperature, under warming or under heating.

Process 2

The compound (Ib) or a salt thereof can be prepared by subjecting the compound (Ia) or a salt thereof to elimination reaction of the carboxyprotective group.

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid including Lewis acid. Suitable base may include an inorganic base and an organic base such as an alkali metal (e.g. sodium, potassium, etc.), an alkaline earth metal (e.g. magnesium calcium, etc.), the hydroxide or carbonate or bicarbonate thereof, trialkylamine (e.g. trimethylamine, triethylamine, etc.) or the like.

Suitable acid may include an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, etc.).

Reduction can be applied preferably for elimination of the protective group such as 4-nitrobenzyl, 2-iodoethyl, 2,2,2-trichloroethyl, or the like. The reduction method applicable for the elimination reaction may include, for example reduction by using a combination of a metal (e.g. zinc, zinc amalgam, etc.) or a salt of chrome compound/e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The reaction is usually carried out in a solvent such as water, an alcohol (e.g. methanol, ethanol, etc.), methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

Process 3

The compound (Ic) or a salt thereof can be prepared by reacting the compound (II) or a salt thereof with the compound (XIV) or a salt thereof.

The reaction is carried out in the presence of a reducing agent such as alkaline metal cyanoborohydride (e.g., sodium cyanoborohydride, etc.) alkaline metal borohydride (e.g., sodium borohydride, etc.), diborane or the like.

The reaction is usually carried out in a solvent such as alcohol (e.g. methanol, ethanol, etc.), methylene chloride, tetrahydrofuran, chloroform, a mixture thereof or any other solvent which does not adversely influence the reaction. The reaction temperature is not critical and the reaction is usually carried out under cooling to warming.

Process 4

The compound (Ie) or a salt thereof can be prepared by subjecting the compound (Id) or a salt thereof to deacylation reaction.

The present deacylation reaction is carried out in accordance with a conventional method such as hydrolysis; reduction; or the like.

This reaction is carried out according to a similar manner to that of Process B-②, and therefore the reaction conditions can be referred to said Process B-②.

Process 5

The compound (Ig) or a salt thereof can be prepared by subjecting the compound (If) or a salt thereof to elimination reaction of the amino protective group.

The present elimination reaction is carried out in accordance with a conventional method such as hydrolysis; reduction; or the like.

This reaction is carried out according to a similar manner to that of Process B-②, and therefore the reaction conditions can be referred to said Process B-②.

Process 6

The compound (Id) or a salt thereof can be prepared by reacting the compound (Ie) or a salt thereof with an acylating agent.

The acylating agent may include an organic acid (i.e. $R_a^2$—OH in which $R_a^2$ is an acyl group) or its reactive derivative or a salt thereof.

The suitable reactive derivative of the organic acid may be a conventional one such as an acid halide (e.g. acid chloride, acid bromide, etc.), an acid azide, an acid anhydride, an activated amide, an activated ester, an isocyanate [e.g. aryl isocyanate (e.g. phenyl isocyanate, etc.), etc.].

When free acid is used as an acylating agent, the acylation reaction may preferably be conducted in the presence of a conventional condensing agent such as N,N'-dicyclohexylcarbodiimide or the like.

The reaction can preferably be conducted in the presence of an inorganic or organic base as exemplified in the explanation of Process B-②.

This reaction is usually carried out in a solvent which does not adversely influence the reaction such as methanol, ethanol, propanol, dichloromethane, tetrahydrofuran, chloroform and the like.

The reaction temperature is not critical and the reaction can be carried out under cooling to under heating.

Process A-①

The compound (VI) or a salt thereof can be prepared by reacting the compound (IV) or a salt thereof with the compound (V).

The reaction is usually carried out in a conventional solvent such as dichloromethane, or any other solvent which does not adversely influence the reaction.

The reaction is preferably carried out in the presence of inorganic or organic base as exemplified in the explanation of Process B-②.

Process A-②

The compound (VIII) or a salt thereof can be prepared by reacting the compound (VI) or a salt thereof with the compound (VII).

The reaction is usually carried out in a conventional solvent such as dimethyl sulfoxide or any other solvent which does not adversely influence the reaction.

The reaction temperature is not critical and the reaction is usually carried out under warming to heating.

Process A-③

The compound (IX) or a salt thereof can be prepared by subjecting the compound (VIII) or a salt thereof to hydrogenation. This reaction is usually carried out in the presence of catalysts such as palladium on carbon or the like.

The reaction is usually carried out in a conventional solvent such as alcohol (e.g. methanol, ethanol, etc.), or any other solvent which does not adversely influence the reaction.

The reaction temperature is not critical and the reaction is usually carried out under cooling to heating.

Process A-④

The compound (Xa) or a salt thereof can be prepared by reacting the compound (IX) or a salt thereof with an acylating agent.

This reaction is carried out by substantially the same method as that of Process 6, and therefore the reaction conditions are to be referred to said Process 6.

Process A-⑤

The compound (XIa) or a salt thereof can be prepared by reducing the compound (Xa) or a salt thereof.

The reduction is usually carried out by using a reducing agent such as di(lower)alkylaluminum hydride (e.g., diisobutylaluminum hydride, etc.), alkali metal aluminum hydride (e.g., lithium aluminum hydride, sodium aluminum hydride, potassium aluminum hydride, etc.) or the like.

The reaction is usually carried out in a conventional solvent such as toluene, tetrahydrofuran, or any other solvent which does not adversely influence the reaction.

The reaction temperature is not critical and the reaction is usually carried out under cooling or ambient temperature.

Process B-①

The compound (XIII) or a salt thereof can be prepared by reacting the compound (XI) or a salt thereof with the compound (XII) or a salt thereof.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide or any other solvent which does not adversely influence the reaction.

The reaction temperature is not critical and the reaction is usually carried out under cooling to heating.

Process B-②

The compound (II) or a salt thereof can be prepared by subjecting the compound (XIII) or a salt thereof to elimination reaction of the imino protective group.

The present elimination reaction is carried out in accordance with a conventional method such as hydrolysis; reduction; or the like. The hydrolysis may include a method using an acid or base and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of the protective group to be eliminated. When the elimination reaction is conducted with the acid, it can be carried out in the presence or absence of a solvent. Suitable solvent may include a conventional organic solvent (e.g., methanol, ethanol, tetrahydrofuran, etc.), water or a mixture thereof.

The hydrolysis with a base is preferably applied for eliminating acyl group, for example, haloalkanoyl (e.g. dichloroacetyl, trifluoroacetyl, etc.), etc.

Suitable base may include for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, cesium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.) or the like. The hydrolysis using a base is often carried out in water, a conventional organic solvent or a mixture thereof. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.) or the like. Suitable reduction may include, for example, reduction with an alkali metal borohydride (e.g. sodium borohydride, etc.) and the like.

The reaction temperature is not critical and may be suitably selected in accordance with the kind of the imino protective group and the elimination method as mentioned above, and the present reaction is preferably carried out under a mild condition such as under cooling, at ambient temperature or slightly elevated temperature.

The object compound (I) of this invention and pharmaceutically acceptable salts thereof are thromboxane $A_2(TXA_2)$ antagonists and $TXA_2$ synthetase inhibitors.

For illustration purpose, some biological data of the object compound (I) are shown in the followings.

In the following test, the used 9,11-methanoepoxy $PGH_2(U46619)$ is characterized pharmacologically as $TXA_2$ mimetic agent and widely used for evaluating $TXA_2$ antagonism of test compounds (for example, vide The Journal of Pharmacology and Experimental Therapeutics Vol. 234, pp 435–441).

Test compound (2S,4R)-2-[(Z)-5-Carboxy-1-pentenyl]-4-(4-chlorophenylsulfonylamino)-1-(3-pyridylmethyl)pyrrolidine [hereinafter referred to as test compound (1)]

Test 1

Inhibition of $TXA_2$ synthetase (a) Test method:

Aspirin treated human platelet microsome (APM, Ran Biochem, Israel) was used as a source of $TXA_2$ synthetase. APM was suspended in 50 mM Tris/100 mM NaCl buffer (pH 7.5). 10 µl of test compound solution was added to 90 µl of APM suspension and incubated at 25° C. for 3 min. And then, 2 µl of $PGH_2$ (10 µg/ml in aceton, Ran Biochem.) was added. After 3-min incubation period, the reaction was terminated by adding 10 µl of $FeCl_2$ solution (25 mM in $H_2O$), and set aside at room temperature for 15 min and then on ice. The reaction mixture was centrifuged at 10000 rpm for 5 min at 4° C. $TXB_2$ in the supernatant was measured by radioimmunoassay. $IC_{50}$ (Inhibition concentration of $TXB_2$ generation by 50%) were graphically determined.

(b) Test result:

$IC_{50}$ of test compound (1): $4.6 \times 10^{-8}$(M)

Test 2

Inhibition of human platelet aggregation induced by U46619

(a) Test method:

Human blood was obtained from healthy male volunteers and mixed with 3.8% (w/v) sodium citrate in a ratio of 9:1. Platelet rich plasma (PRP) was prepared from the citrated blood by centrifugation at 150×g for 15 min. Platelet aggregation in PRP was studied photometrically using an aggregometer (NKK HAEMATRACER 1). To the 225 µl of PRP, 25 µl of test compound solution was added, and then stirred at 1000 rpm for 2 min at 37° C. To the solution, 5 µl of U46619 (final 1.0 µM) was added as an aggregating inducer. $IC_{50}$ (Inhibition concentration of platelet aggregation by 50%) were determined graphically.

(b) Test result:

$IC_{50}$ of test compound (1): $2.7 \times 10^{-7}$ (M)

The object compound (I) or its pharmaceutically acceptable salts can usually be administered to mammals including human being in the form of a conventional pharmaceutical composition such as capsule, micro-capsule, tablet, granule, powder, troche, syrup, aerosol, inhalation, solution, injection, suspension, emulsion, suppository, ointment, nasal drop, eye drop, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

To a solution of (2S,4R)-1-t-butoxycarbonyl-4-hydroxy-2-methoxycarbonylpyrrolidine (53.4 g) in dichloromethane (500 ml) were added triethylamine (36 ml) and methanesulfonyl chloride (19.8 ml) under ice bath cooling and the mixture was stirred at the same temperature for 3 hours. The solution was washed successively with diluted hydrochloric acid, saturated aqueous sodium bicarbonate and brine and dried over magnesium sulfate. The solvent was evaporated in vacuo and the residue was crystallized from n-hexane to give (2S,4R)-1-t-butoxycarbonyl-4-methylsulfonyloxy-2-methoxycarbonylpyrrolidine (56.2 g) as colorless crystal.

mp: 73°–75° C.

$^1$H-NMR (CDCl$_3$) δ ppm: 1.43 (9×2/3H, s), 1.47 (9×1/3H, s), 2.28 (1H, ddd, J=5, 8, 14 Hz), 2.63 (1H, m), 3.05 (3H, s), 3.7–3.9 (2H, m), 3.77 (3H, s), 4.41 (2/3H, t, J=8 Hz), 4.48 (1/3H, t, J=8 Hz), 5.28 (1H, m)

Preparation 2

A mixture of (2S,4R)-1-t-butoxycarbonyl-4-methylsulfonyloxy-2-methoxycarbonylpyrrolidine (32.3 g) and sodium benzoate (28.8 g) in dimethyl sulfoxide (320 ml) was stirred at 90° C. overnight and cooled to room temperature. The mixture was diluted with ethyl acetate (600 ml) and washed successively with water and brine. The organic phase was dried over magnesium sulfate and the solvent was evaporated in vacuo to give an oil. The oil was crystallized from n-hexane to give (2S,4S)-4-benzoyloxy-1-t-butoxycarbonyl-2-methoxycarbonylpyrrolidine (31.0 g) as a colorless crystal.

mp: 89°–90° C.

$^1$H-NMR (CDCl$_3$) δ ppm: 1.45 (9/2H, s), 1.48 (9/2H, s), 2.4–2.7 (2H, m), 3.68 (3/2H, s), 3.69 (3/2H, s), 3.69 (1H, m), 3.82 (1H, m), 4.48 (1/2H, dd, J=2, 11 Hz), 4.61 (1/2H, dd, J=4, 11 Hz), 5.53 (1H, m), 7.43 (1H, t, J=7.5 Hz), 7.57 (2H, t, J=7.5 Hz), 7.98 (2H, d, J=7.5 Hz)

Preparation 3

To a solution of (2S,4S)-4-benzoyloxy-1-t-butoxycarbonyl-2-methoxycarbonylpyrrolidine (30.0 g) in methanol (600 ml) was added potassium carbonate (11.9 g) and the mixture was stirred at room temperature for 1 hour. The solution was diluted with ethyl acetate (1 l) and washed with water. The organic phase was washed with brine. The aqueous phase was saturated with sodium chloride, extracted with chloroform and washed with brine. The combined organic extracts were dried over magnesium sulfate and evaporated in vacuo to give an oil. The oil was chromatographed on a silica gel (500 g) column with a mixture of n-hexane and ethyl acetate (1:1) as an eluent to give (2S,4S)-1-t-butoxycarbonyl-4-hydroxy-2-methoxycarbonylpyrrolidine (20.7 g) as colorless crystal.

mp: 59°–62° C.

$^1$H-NMR (CDCl$_3$) δ ppm: 1.45 (9×3/5H, s), 1.47 (9×2/5H, s), 2.10 (1H, m), 2.33 (1H, m), 3.5–3.7 (3H, m), 3.78 (3×3/5H, s), 3.80 (3×2/5H, s), 4.35 (1H, m)

Preparation 4

To a solution of (2S,4S)-1-t-butoxycarbonyl-4-hydroxy-2-methoxycarbonylpyrrolidine (20.0 g) in dichloromethane (500 ml) were added triethylamine (13.5 ml) and methanesulfonyl chloride (7.4 ml) with stirring in an ice bath and the mixture was stirred at the same temperature for 4 hours. The solution was washed successively with diluted hydrochloric acid, saturated aqueous sodium bicarbonate and brine and dried over magnesium sulfate. The solvent was evaporated in vacuo to give (2S,4S)-1-t-butoxycarbonyl-4-methylsulfonyloxy-2-methoxycarbonylpyrrolidine (27.7 g) as a pale brown oil.

$^1$H-NMR (CDCl$_3$) δ ppm: 1.43 (9×3/5H, s), 1.46 (9×2/5H, s), 2.53 (2H, m), 3.03 (3H, s), 3.76 (3H, s), 3.80 (2H, m), 4.4–4.6 (1H, m), 5.75 (1H, m)

Preparation 5

A mixture of (2S,4S)-1-t-butoxycarbonyl-4-methylsulfonyloxy-2-methoxycarbonylpyrrolidine (27.7 g) and sodium azide (10.6 g) in dimethyl sulfoxide (350 ml) was stirred at 90° C. overnight and the solution was diluted with ethyl acetate (600 ml). The solution was washed successively with water and brine and dried over magnesium sulfate. The solvent was evaporated in vacuo to give (2S,4R)-4-azido-1-t-butoxycarbonyl-2-methoxycarbonylpyrrolidine (20.0 g) as a pale brown oil.

$^1$H-NMR (CDCl$_3$) δ ppm: 1.41 (9×2/3H, s), 1.47 (9×1/3H, s), 2.20 (1H, m), 2.32 (1H, m), 3.4–3.7 (3H, m), 3.76 (3H, s), 4.20 (1H, m), 4.36 (1H, m)

Preparation 6

A solution of (2S,4R)-4-azido-1-t-butoxycarbonyl-2-methoxycarbonylpyrrolidine (112 g) in methanol (870 ml) was hydrogenated under ambient pressure for 5 hours in the presence of 10% palladium on carbon (20.2 g).

After removal of the catalyst by filtration, the filtrate was evaporated in vacuo to give (2S,4R)-4-amino-1-t-butoxycarbonyl-2-methoxycarbonylpyrrolidine (93.8 g) as an oil.

$^1$H-NMR (CDCl$_3$) δ ppm: 1.41 (9×2/3H, s), 1.46 (9×1/3H, s), 1.9–2.2 (2H, m), 3.2–3.4 (1H, m), 3.6–3.8 (2H, m), 3.74 (3H, s), 4.40 (1H, m)

Preparation 7

To a solution of (2S,4R)-4-amino-1-t-butoxycarbonyl-2-methoxycarbonylpyrrolidine (6.04 g) in dichloromethane (60 ml) were added triethylamine (3.44 ml) and p-chlorobenzenesulfonyl chloride (6.26 g) in an ice bath. After being stirred at room temperature overnight, the solution was washed successively with diluted hydrochloric acid, saturated aqueous sodium bicarbonate and brine and dried over magnesium sulfate. The solvent was evaporated in vacuo and the residue was crystallized from n-hexane to give (2S,4R)-1-t-butoxycarbonyl-4-(4-chlorophenylsulfonylamino)-2-methoxycarbonylpyrrolidine (9.13 g) as a pale yellow crystal.

$^1$H-NMR (CDCl$_3$) δ ppm: 1.37 (9×2/3H, s), 1.40 (9×1/3H, s), 2.0–2.4 (2H, m), 3.20 (1H, m), 3.63 (1H, m), 3.95 (1H, m), 4.30 (1H, m), 5.0–5.2 (1H, m), 7.52 (2H, d, J=10 Hz), 7.83 (2H, d, J=10 Hz)

Preparation 8

To a solution of (2S,4R)-1-t-butoxycarbonyl-4-(4-chlorophenylsulfonylamino)-2-methoxycarbonylpyrrolidine (9.01 g) in toluene (70 ml) was added dropwise 1.5 molar solution of diisobutylaluminum hydride (61.2 m mol) in tetrahydrofuran (40.8 ml) at −78° C. After the mixture was stirred at −78° C. for 1.5 hours, saturated aqueous potassium sodium tartrate was added to the reaction mixture and the mixture was filtered through Celite. The solid was washed with ethyl acetate and the combined organic solution was washed with brine and dried over magnesium sulfate. The solvent was evaporated in vacuo and the residue was chromatographed on a silica gel column with a mixture of ethyl acetate and n-hexane (1:2–2:1) as an eluent to give (2S,4R)-1-t-butoxycarbonyl-4-(4-chlorophenylsulfonylamino)-2-formylpyrrolidine (5.51 g) as pale yellow crystal.

mp: 120°–122° C.

$^1$H-NMR (CDCl$_3$) δ ppm: 1.43 (9H, s), 2.16 (2H, m), 3.33 (1H, m), 3.60 (1H, m), 3.85 (1H, m), 4.26 (1H, m), 4.87 (1H, m), 7.53 (2H, d, J=10 Hz), 7.82 (2H, d, J=10 Hz), 9.4–9.6 (1H, m)

Preparation 9

To a suspension of triphenyl-(4-methoxycarbonylbenzyl)phosphonium chloride (88.49 g) in tetrahydrofuran (500 ml) was added sodium hydride (4.75 g) by portions under an ice bath cooling and the mixture was stirred in an ice bath for 1 hour.

To the resulting yellow suspension was added dropwise a solution of (2S,4R)-1-t-butoxycarbonyl-4-(4-chloro-phenylsulfonylamino)-2-formylpyrrolidine (70.0 g) in tetrahydrofuran (200 ml) under ice bath cooling and the mixture was stirred in an ice bath for 1 hour. To the mixture were added saturated aqueous ammonium chloride (50 ml) and ethyl acetate (1.5 l) and the solution was washed successively with water and brine. The organic layer was dried over magnesium sulfate and the solvent was evaporated in vacuo to give a crude (2S,4R)-1-t-butoxycarbonyl-4-(4-chlorophenylsulfonylamino)-2-[(E and Z)-2-(4-methoxycarbonylphenyl)vinyl]pyrrolidine. The crude product was separated by using a silica gel (1 kg) column with a mixture of n-hexane and ethyl acetate (4:1–2:1) as an eluent to give (2S,4R)-1-t-butoxycarbonyl-4-(4-chlorophenylsulfonylamino)-2 -[(Z)-2-(4-methoxycarbonylphenyl)vinyl]pyrrolidine (Z isomer, 15.98 g, less polar) as a white powder and (2S,4R)-1-t-butoxycarbonyl-4 -(4-chlorophenylsulfonylamino)-2-[(E)-2-(4-methoxycarbonylphenyl)vinyl]pyrrolidine (E isomer, 21.94 g, more polar) as a white powder.
Z isomer mp: 178°–179° C. $^1$H-NMR (CDCl$_3$) δ ppm: 1.29 (9H, s), 1.8–2.3 (2H, m), 3.26 (1H, m), 3.51 (1H, dd, J=6, 11 Hz), 3.89 (1H, m), 3.93 (3H, s), 4.78 (1H, m), 5.10 (1H, m), 5.60 (1H, dd, J=9, 11.5 Hz), 6.48 (1H, d, J=11.5 Hz), 7.2–7.4 (2H, m), 7.48 (2H, d, J=8.5 Hz), 7.82 (2H, d, J=8.5 Hz), 8.02 (2H, d, J=8.5 Hz)

E isomer mp: 164°–165° C. $^1$H-NMR (CDCl$_3$) δ ppm: 1.39 (9H, s), 1.9–2.2 (2H, m), 3.24 (1H, dd, J=5, 11 Hz), 3.55 (1H, dd, J=6, 11.5 Hz), 3.91 (3H, s), 3.8–4.0 (1H, m), 4.49 (1H, m), 4.91 (1H, m), 6.12 (1H, dd, J=6.5, 15.5 Hz), 7.37 (2H, d, J=8.5 Hz), 7.50 (2H, d, J=8.5 Hz), 7.82 (2H, d, J=8.5 Hz), 7.97 (2H, d, J=8.5 Hz)

Preparation 10

The following compounds were obtained according to similar manner to that of Preparation 9.

(2S,4R)-1-t-Butoxycarbonyl-4-(4-chlorophenylsulfonylamino)-2 -[(Z)-2-(3-methoxycarbonylphenyl)vinyl]pyrrolidine mp: 154°–156° C. $^1$H-NMR (CDCl$_3$) δ ppm: 1.28 (9H, s), 1.8–2.1 (2H, m), 3.30 (1H, dd, J=5, 12 Hz), 3.56 (1H, dd, J=6, 12 Hz), 3.89 (1H, m), 3.93 (3H, s), 4.79 (1H, m), 4.93 (1H, d, J=7 Hz), 5.58 (1H, dd, J=9, 12.5 Hz), 6.48 (1H, d, J=12.5 Hz), 7.3–7.5 (4H, m), 7.83 (2H, d, J=8.5 Hz, 7.92 (2H, m)

(2S,4R)-1-t-Butoxycarbonyl-4-(4-chlorophenyl-sulfonylamino)-2-[ (E)-2-(3-methoxycarbonylphenyl)vinyl]pyrrolidine mp: 126°–128° C. $^1$H-NMR (CDCl$_3$) δ ppm: 1.40 (9H, s), 1.8–2.1 (2H, m), 3.24 , (1H, dd, J=5.5, 11 Hz) 3.57 (1H, dd, J=6, 11 Hz), 3.92 (3H, s), 3.97 (1H, m), 4.49 (1H, m), 4.88 (1H, m), 6.09 (1H, dd, J=6.5, 16 Hz), 6.43 (1H, d, J=16 Hz), 7.49 (1H, t, J=7.5 Hz), 7.4–7.6 (3H, m), 7.33 (2H, d, J=8.5 Hz), 7.92 (1H, d, J=7 Hz), 8.03 (1H, s)

Preparation 11

(1) A solution of (2S,4R)-1-t-butoxycarbonyl-4-(4-chlorophenylsulfonylamino)-2 -[(Z)-2-(4-methoxycarbonylphenyl)vinyl]pyrrolidine (15.5 g) in 90% aqueous trifluoroacetic acid (100 ml) was stirred at room temperature for 30 minutes and the solvent was evaporated in vacuo. The residue was suspended in chloroform (200 ml) and the solution was adjusted to pH 8 with saturated aqueous sodium bicarbonate. The organic phase was separated, washed with brine and dried over magnesium sulfate. The solvent was evaporated in vacuo and the residual solid was collected by filtration to give (2S,4R)-4-(4-chlorophenylsulfonylamino)-2-[(Z)-2-(4 -methoxycarbonylphenyl)vinyl]pyrrolidine (11.9 g) as a white powder.

mp: 189°–190° C. $^1$H-NMR (CDCl$_3$) δ ppm: 1.7–2.2 (2H, m), 2.66 (1H, dd, J=4.5, 11.5 Hz), 3.18 (1H, dd, J=6, 11.5 Hz), 3.88 (1H, m), 3.93 (3H, s), 4.08 (1H, m), 5.61 (1H, dd, J=9.5, 11.5 Hz), 6.52 (1H, d, J=11.5 Hz), 7.28 (2H, d, J=8.5 Hz), 7.49 (1H, d, J=8.5 Hz), 7.80 (1H, d, J=8.5 Hz), 8.00 (2H, d, J=8.5 Hz)

The following compound was obtained according to a similar manner to that of Preparation 11(1).

(2) (2S,4R)-4-(4-Chlorophenylsulfonylamino)-2-[(Z)-2-(3 -methoxycarbonylphenyl)vinyl]pyrrolidine $^1$H-NMR (CDCl$_3$) δ ppm: 1.75 (1H, dd, J=7.5, 14 Hz), 1.91 (1H, m), 2.74 (1H, dd, J=5, 12 Hz), 3.26 (1H, dd, J=6, 12 Hz), 3.90 (1H, m), 3.92 (3H, s), 4.13 (1H, m), 5.62 (1H, dd, J=9.5, 12 Hz), 6.51 (1H, d, J=12 Hz), 7.3–7.5 (5H, m), 7.7–8.0 (3H, m)

Preparation 12

To a suspension of (4-carboxybutyl)triphenylphosphonium bromide (13.3 g) in a mixture of tetrahydrofuran (80 ml) and hexamethylphosphoramide (20 ml) was added a solution (60 ml, 1M solution) of lithium bis(trimethylsilyl)amide in tetrahydrofuran at 0° C. and the solution was stirred at room temperature for 1 hour. After the solution was cooled to −25° C., a solution of (2S,4R)-1-t-butoxycarbonyl-4-(4-chlorophenylsulfonylamino)-2-formylpyrrolidine (3.89 g) in tetrahydrofuran (20 ml) was added dropwise thereto and the solution was stirred at −20° C.–−25° C. for 30 minutes. water (100 ml) and ethyl acetate (100 ml) were added to the solution and the aqueous phase was separated. The aqueous solution was adjusted to pH2 with 1N hydrochloric acid and extracted with ethyl acetate (200 ml). The organic layer was washed two times with water and then with brine and dried over magnesium sulfate. The solvent was evaporated in vacuo and the residue was chromatographed on a silica gel (150 g) column with a mixture of chloroform and methanol (30:1) as an eluent to give (2S, 4R)-1-t-butoxycarbonyl-2-[(Z)-5-carboxy-1-pentenyl]-4-(4-chlorophenylsulfonylamino)pyrrolidine (2.98 g) as a colorless oil.

$^1$H-NMR (CDCl$_3$) δ ppm: 1.42 (9H, s), 1.6–1.8 (3H, m), 2.0–2.2 (3H, m), 2.35–2.45 (2H, m), 3.3–3.45 (2H, m), 3.84 (1H, m), 5.2–5.45 (2H, m), 5.75 (broad, 1H)

Preparation 13

A solution of (2S,4R)-1-t-butoxycarbonyl-2-[(Z)-5-carboxy-1-pentenyl] -4-(4-chlorophenylsulfonylamino)pyrrolidine (2.90 g) in methanol (50 ml) saturated with hydrogen chloride was stirred at room temperature overnight and the solvent was evaporated in vacuo. The residue was dissolved in chloroform (50 ml) and the solution was washed successively with saturated aqueous sodium bicarbonate and brine. The organic layer was dried over magnesium sulfate and the solvent was evaporated in vacuo to give (2S,4R)-4-(4-chlorophenylsulfonylamino)-2 -[(Z)-5-methoxycarbonyl-1-pentenyl]pyrrolidine (2.28 g) as a pale brown oil.

$^1$H-NMR (CDCl$_3$) δ ppm: 1.6–1.9 (m, J=4 Hz), 2.05–2.15 (2H, m), 2.32 (2H, t, J=7.5 Hz), 2.72 (1H, dd, J=4, 12 Hz), 3.23 (1H, dd, J=6, 12 Hz), 3.69 (3H, s), 3.85 (1H, m), 4.00 (1H, q, J=7 Hz), 5.3–5.5 (2H, m), 7.51 (2H, d, J=8.5 Hz), 7.83 (2H, d, J=8.5 Hz)

EXAMPLE 1

(1) A mixture of (2S,4R)-4-(4-chlorophenylsulfonylamino)-2-[ (Z)-5-methoxycarbonyl-1-pentenyl]pyrrolidine (1.00 g), 3-picolylchloride hydrochloride (509 mg) and triethylamine (0.43 ml) in tetrahydrofuran (25 ml) was refluxed for 48 hours and the solution was diluted with chloroform (40 ml). The solution was washed successively with saturated aqueous sodium bicarbonate and brine, and the organic layer was dried over magnesium sulfate. The solvent was evaporated in vacuo and the residue was chromatographed on a silica gel (50 g) column with a mixture of chloroform and methanol (100:1) as an eluent to give (2S,4R)-4-(4-chlorophenylsulfonylamino)-2 -[(Z)-5-methoxycarbonyl-1-pentenyl]-1-(3-pyridylmethyl)pyrrolidine (700 mg) as a pale brown oil.

¹H-NMR (CDCl₃) δ ppm: 1.6–1.9 (3H, m), 2.0–2.15 (3H, m), 2.32 (2H, t, J=7.5 Hz), 3.05–3.2 (2H, m), 3.42 (1H, q, J=7.5 Hz), 3.67 (3H, s), 3.65–3.8 (2H, m), 3.88 (1H, d, J=13.5 Hz), 5.2–5.4 (2H, m), 5.54 (1H, m), 7.22 (1H, m), 7.47 (2H, d, J=8.5 Hz), 7.58 (1H, m), 7.79 (2H, d, J=8.5 Hz), 8.45–8.55 (2H, m)

The following compounds were obtained according to similar manner to that of Example 1(1).

(2) (2S,4R)-4-(4-Chlorophenylsulfonylamino)-2-[(Z)-5-methoxycarbonyl-1-pentenyl]-1-(2-pyridylmethyl)pyrrolidine ¹H-NMR (CDCl₃) δ ppm: 1.55–1.70 (2H, m), 1.75–1.85 (2H, m), 1.9–2.05 (2H, m), 2.22 (2H, t, J=7 Hz), 2.34 (1H, dd, J=5, 10 Hz), 3.23 (1H, dd, J=6.5, 10 Hz), 3.54 (1H, d, J=15 Hz), 3.66 (3H, s), 3.67 (1H, m), 3.73 (1H, m), 4.01 (1H, d, J=15 Hz), 5.27 (1H, t, J=10 Hz), 5.48 (1H, dt, J=7.5, 10 Hz), 6.80 (1H, d, J=8 Hz), 7.15–7.25 (2H, m), 7.4–7.8 (5H, m), 8.57 (1H, m) (3) (2S,4R)-4-(4-Chlorophenylsulfonylamino)-2-[(Z)-5-methoxycarbony- 1-1-pentenyl]-1-(4-pyridylmethyl)pyrrolidine ¹H-NMR (CDCl₃) δ ppm: 1.6–1.9 (4H, m), 2.0–2.15 (2H, m), 2.31 (2H, t, J=7 Hz), 3.05–3.15 (2H, m), 3.42 (1H, m), 3.67 (1H, m), 3.68 (3H, s), 3.77 (1H, m), 3.85 (1H, d, J=14 Hz), 5.2–5.4 (2H, m), 5.51 (1H, dt, J=7.5, 10.5 Hz), 7.16 (2H, d, J=5.5 Hz), 7.44 (2H, d, J=8.5 Hz), 7.78 (2H, d, J=8.5 Hz), 8.49 (2H, d, J=5.5 Hz)

(4) (2S,4R)-4-(4-Chlorophenylsulfonylamino)-2-[(Z)-2-(4-methoxycarbonylphenyl)vinyl]-1-(3-pyridylmethyl)pyrrolidine ¹H-NMR (CDCl₃) δ ppm: 1.9–2.2 (3H, m), 3.10 (1H, t, J=8 Hz), 3.14 (1H, d, J=13.5 Hz), 3.57 (1H, q, J=9 Hz), 3.80 (1H, d, J=13.5 Hz), 3.82 (1H, m), 3.95 (3H, s), 5.32 (1H, broad), 5.66 (1H, dd, J=9, 11 Hz), 6.62 (d, J=11 Hz), 7.1–7.2 (3H, m), 7.4–7.5 (3H, m), 7.76 (2H, d, J=9 Hz), 7.98 (2H, d, J=8 Hz), 8.35 (1H, m), 8.44 (1H, m)

(5) (2S,4R)-4-(4-Chlorophenylsulfonylamino)-2-[(Z)-2-(3-methoxycarbonylphenyl)vinyl]-1-(3-pyridylmethyl)pyrrolidine ¹H-NMR (CDCl₃) δ ppm: 1.9–2.2 (3H, m), 3.0–3.15 (2H, m), 3.56 (1H, q, J=8 Hz), 3.83 (1H, d, J=13.5 Hz), 3.86 (1H, m), 3.92 (3H, s), 5.45 (1H, d, J=8 Hz), 5.62 (1H, dd, J=9.5, 11 Hz), 6.62 (1H, d, J=11 Hz), 7.15 (1H, dd, J=4.5, 7 Hz), 7.3–7.5 (5H, m), 7.7–8.0 (4H, m), 8.37 (1H, m), 8.44 (1H, m)

EXAMPLE 2

(1) A solution of (2S,4R)-4-(4-chlorophenylsulfonylamino)-2-[(Z)-5-methoxycarbonyl-1-pentenyl]-1-(3-pyridylmethyl)pyrrolidine (670 mg) in a mixture of methanol (5 ml) and 1N-aqueous sodium hydroxide (3 ml) was stirred at room temperature for 4 hours. The solution was adjusted to pH 5 with 10% hydrochloric acid and extracted with chloroform, and the organic solution was washed with brine. The solution was dried over magnesium sulfate and the solvent was evaporated in vacuo. The residue was chromatographed on a silica gel (20 g) column with a mixture of chloroform and methanol (20:1) as an eluent to give (2S,4R)-2-[(Z)-5-carboxy-1-pentenyl]-4-(4-chlorophenylsulfonylamino)-1-(3-pyridylmethyl)pyrrolidine (408 mg) as a pale yellow amorphous.

¹H-NMR (CDCl₃) δ ppm: 1.6–1.75 (2H, m), 1.8–1.9 (2H, m), 2.1–2.25 (2H, m), 2.38 (2H, m), 3.13 (1H, dd, J=7.5, 10 Hz), 3.41 (1H, d, J=13.5 Hz), 3.67 (1H, q, J=8 Hz), 3.82 (1H, m), 3.94 (1H, d, J=13.5 Hz), 5.36 (1H, t, J=10 Hz), 5.62 (1H, dt, J=10, 11.5 Hz), 7.34 (1H, m), 7.42 (2H, d, J=8.5 Hz), 7.74 (1H, m), 7.76 (2H, d, J=8.5 Hz), 8.45–8.55 (2H, m).

The following compounds were obtained according to a similar manner to that of Example 2(1).

(2) (2S,4R)-2-[(Z)-5-Carboxy-1-pentenyl]-4-(4-chlorophenylsulfonylamino)-1-(2-pyridylmethyl)pyrrolidine (3) (2S,4R)-2-[(Z)-5-Carboxy-1-pentenyl]-4-(4-chlorophenylsulfonylamino)-1-(4-pyridylmethyl)pyrrolidine (4) (2S,4R)-2-[(Z)-2-(4-Carboxyphenyl)vinyl]-4-(4-chlorophenylsulfonylamino)-1-(3-pyridylmethyl)pyrrolidine ¹H-NMR (DMSO-d₆) δ ppm: 1.80 (2H, t, J=6.5 Hz), 1.90 (1H, t, J=8.5 Hz), 2.83 (1H, t, J=8.5 Hz), 3.12 (1H, d, J=13.5 Hz), 3.35–3.65 (3H, m), 3.68 (1H, d, J=13.5 Hz), 5.62 (1H, dd, J=11.5, 9 Hz), 6.62 (1H, d, J=11.5 Hz), 7.24 (1H, dd, J=4.5, 7.5 Hz), 7.31 (2H, d, J=7.5 Hz), 7.44 (1H, d, J=7.5 Hz), 7.62 (2H, d, J=8.5 Hz), 7.88 (2H, d, J=8.5 Hz), 7.94 (2H, d, J=7.5 Hz), 8.03 (1H, m, 8.28 (1H, s), 8.39 (1H, d, J=4.5 Hz)

(5) (2S,4R)-2-[(Z)-2-(3-Carboxyphenyl)vinyl]-4-(4-chlorophenylsulfonylamino)-1-(3-pyridylmethyl)pyrrolidine ¹H-NMR (DMSO-d₆) δ ppm: 1.78 (2H, t, J=6.5 Hz), 1.90 (1H, t, J=8.5 Hz), 2.72 (1H, t, J=8.5 Hz), 3.13 (1H, d, J=13.5 Hz), 3.3–3.6 (2H, m), 3.72 (1H. d, J=13.5 Hz), 5.60 (1H, dd, J=11.5, 9 Hz), 6.62 (1H, d, J=11.5 Hz), 7.20 (1H, dd, J=4, 7.5 Hz), 7.4–7.6 (3H, m), 7.64 (2H, d, J=8 Hz), 7.75–7.9 (4H, m), 8.06 (1H, d, J=7.5 Hz), 8.27 (1H, m), 8.38 (1H, m)

EXAMPLE 3

(1) A solution of (2S,4R)-2-[(Z)-5-carboxy-1-pentenyl]-4-(4-chlorophenylsulfonylamino)-1-(3-pyridylmethyl)pyrrolidine (104 mg) in ethyl acetate (5 ml) was added 1N-hydrogen chloride in ethyl acetate (0.25 ml) and the precipitated brown solid was collected and dried in vacuo to give (2S,4R)-2-[(Z)-5-carboxy-1-pentenyl]-4-(4-chlorophenylsulfonylamino)-1-(3-pyridylmethyl)pyrrolidine hydrochloride (100 mg) as a brown powder.

¹H-NMR (D₂O-DCl) δ ppm: 1.5–1.65 (2H, m), 1.95–2.15 (4H, m), 2.24 (2H, t, J=6.5 Hz), 3.18 (1H, dd, J=5.5, 12.5 Hz), 3.60 (1H, dd, J=7.5, 12.5 Hz), 4.02 (1H, m), 4.5–4.7 (2H, m), 5.33 (1H, t, J=10 Hz), 5.83 (1H, dt, J=10, 11.5 Hz), 7.51 (2H, d, J=8 Hz) 7.83 (2H, d, J=8 Hz) 8.08 (1H, dd, J=5.5, 8 Hz), 8.63 (1H, m), 8.82 (1H, d, J=5.5 Hz), 8.90 (1H, s)

The following compounds were obtained according to a similar manner to that of Example 3(1).

(2) (2S,4R)-2-[(Z)-5-Carboxy-1-pentenyl]-4-(4chlorophenylsulfonylamino)-1-(2-pyridylmethyl)pyrrolidine hydrochloride ¹H-NMR (D₂O-DCl) δ ppm: 1.4–1.6 (2H, m), 1.85–2.05 (4H, m ), 2.17 (2H, t, J=7 Hz), 3.20 (1H, dd, J=5, 12.5 Hz), 3.62 (1H, dd, J=8, 12.5 Hz), 3.94 (1H, m), 4.5–4.65 (3H, m), 5.21 (1H, t, J=10 Hz), 5.77 (1H, dt, J=7.5, 10 Hz), 7.44 (2H, d, J=8.5 Hz), 7.68 (2H, d, J=8.5 Hz), 7.85–7.95 (2H, m), 8.41 (1H, dt, J=1, 8.5 Hz), 8.70 (1H, m)

(3) (2S,4R)-2-[(Z)-5-Carboxy-1-pentenyl]-4-(4-chlorophenylsulfonylamino)-1-(4-pyridylmethyl)pyrrolidine hydrochloride ¹H-NMR (D₂O-DCl) δ ppm: 1.45–1.55 (2H, m), 1.85–2.0 (4H, m), 2.13 (2H, t, J=7.5 Hz), 3.04 (1H, dd, J=5.5, 12 Hz), 3.49 (1H, dd, J=7.5, 12 Hz), 3.91 1H, m), 4.4–4.65 (3H, m), 5.23 (1H, t, J=10 Hz), 5.75 (1H, dt, J=10, 7.5 Hz), 7.40 (2H, d, J=8.5 Hz), 7.62 (2H, d, J=8.5 Hz), 7.97 (2H, d, J=6.5 Hz), 8.70 (2H, d, J=6.5 Hz)

Preparation 14

The following compounds were obtained according to similar manner to that of Preparation 12.

(1) (2S,4R)-1-t-Butoxycarbonyl-2-[(Z)-4-carboxy-1-butenyl] -4-(4-chlorophenylsulfonylamino)pyrrolidine ¹H-NMR (CDCl₃) δ ppm: 1.40 (9H, s), 1.7–1.85 (3H, m), 2.3–2.5 (4H, m), 3.3–3.45 (2H, m), 3.85 (1H, m), 5.28 (1H, t, J=10 Hz), 5.42 (1H, dt, J=10, 7 Hz), 7.50 (2H, d, J=8.5 Hz), 7.83 (2H, d, J=8.5 Hz)

(2) (2S,4R)-1-t-Butoxycarbonyl-2-[(Z)-5-carboxy-1-pentenyl]-4-phenylsulfonylaminopyrrolidine ¹H-NMR (CDCl₃) δ ppm: 1.40 (9H, s), 1.6–1.8 (3H, 2.05–2.2 (3H, m), 2.38 (2H, t, J=7 Hz), 3.29 (1H, dd, J=3, 11 Hz), 3.42 (1H, dd, J=5.5, 11 Hz), 3.85 (1H, m), 4.58 (1H, m), 5.2–5.45 (2H, m), 5.77 (1H, d, J=6 Hz), 7.5–7.65 (3H, m), 8.85–8.95 (2H, m)

Preparation 15

The following compounds were obtained according to a similar manner to that of Preparation 13.

(1) (2S,4R)-4-(4-Chlorophenylsulfonylamino)-2-[(Z)-4-methoxycarbonyl-1-butenyl]pyrrolidine (2) (2S,4R)-2-[(Z)-5-Methoxycarbonyl-1-pentenyl]-4-phenylsulfonylaminopyrrolidine ¹H-NMR (CDCl₃) δ ppm: 1.55–1.6 (3H, m), 1.82 (1H, ddd, J=3, 7, 14 Hz), 2.09 (2H, q, J=7.5 Hz), 2.29 (2H, t, J=7.5 Hz), 2.73 (1H, dd, J=4, 11 Hz), 3.21 (1H, dd, J=5.5, 11 Hz), 3.67 (3H, s), 3.85 (1H, m), 4.02 (1H, q, J=7.5 Hz), 5.25–5.5 (2H, m), 7.45–7.6 (3H, m), 7.85–7.9 (2H, m)

EXAMPLE 4

The following compounds were obtained according to a similar manner to that of Example 1 (1).

(1) (2S,4R)-4-(4-Chlorophenylsulfonylamino)-2-[(Z)-5-methoxycarbonyl-1-pentenyl]-1-(2-quinolylmethyl)pyrrolidine ¹H-NMR (CDCl₃) δ ppm: 1.5–1.65 (2H, m), 1.8–2.05 (4H, m), 2.18 (2H, t, J=7 Hz), 2.41 (1H, dd, J=4.5, 10.5 Hz), 3.26 (1H, dd, J=6, 10.5 Hz), 3.62 (3H, s), 3.6–3.95 (3H, m), 4.17 (1H, d, J=15 Hz), 5.29 (1H, t, J=10 Hz), 5.50 (1H, m), 6.34 (1H, d, J=7.5 Hz), 7.3–7.4 (2H, m), 7.4–7.6 (2H, m), 7.7–7.85 (4H, m), 8.11 (1H, d, J=8.5 Hz), 8.21 (1H, d, J=8.5 Hz)

(2) (2S,4R)-1-(2-Benzothiazolylmethyl)-4-(4-chlorophenylsulfonylamino)-2-[(Z)-5-methoxycarbonyl-1-pentenyl]pyrrolidine ¹H-NMR (CDCl₃) δ ppm: 1.59 (2H, m), 1.7–2.0 (4H, m), 2.08 (2H, t, J=7 Hz), 2.55 (1H, dd, J=4, 10 Hz), 3.40 (1H, dd, J=6, 10 Hz), 3.62 (3H, s), 3.92 (2H, m), 4.05 (1H, d, J=16 Hz), 4.26 (1H, d, J=16 Hz), 5.27 (1H, t, J=10 Hz), 5.53 (1H, dt, J=10, 7 Hz), 6.96 (1H, d, J=8 Hz), 7.35–7.55 (4H, m), 7.78 (2H, d, J=8.5 Hz), 7.88 (1H, d, J=8 Hz), 8.17 (1H, d, J=8 Hz)

(3) (2S,4R)-1-(2-Benzoxazolylmethyl)-4-(4-chlorophenylsulfonylamino)-2-[(Z)-5-methoxycarbonyl-1-pentenyl]pyrrolidine ¹H-NMR (CDCl₃) δ ppm: 1.60 (2H, m), 1.7–2.0 (4H, m), 2.11 (2H, t, J=7 Hz), 2.57 (1H, dd, J=2, 10 Hz), 3.40 (1H, dd, J=7, 10 Hz), 3.61 (3H, s), 3.90 (2H, m), 3.99 (1H, d, J=16 Hz), 4.18 (1H, d, J=16 Hz), 5.27 (1H, t, J=10 Hz), 5.53 (1H, dt, J=10, 7 Hz), 7.3–7.5 (4H, m), 7.50 (1H, m), 7.76 (1H, d, J=8.5 Hz), 7.80 (1H, m)

(4) (2S,4R)-2-[(Z)-5-Methoxycarbonyl-1-pentenyl]-4-phenylsulfonylamino-1-(3-pyridylmethyl)pyrrolidine ¹H-NMR (CDCl₃) δ ppm: 1.65–2.0 (5H, m), 2.08 (2H, q, J=8 Hz), 2.30 (2H, t, J=7 Hz), 3.07 (1H, t, J=8 Hz), 3.12 (1H, d, J=13.5 Hz), 3.35 (1H, q, J=8 Hz), 3.69 (3H, s), 3.77 (1H, m), 3.85 (1H, d, J=13.5 Hz), 5.18 (1H, d, J=8 Hz), 5.28 (1H, t, J=10 Hz), 5.52 (1H, dt, J=10, 7 Hz), 7.21 (1H, dd, J=4.5, 7 Hz), 7.45–7.55 (4H, m), 7.8–7.85 (2H, m), 8.42 (1H, m), 8.47 (1H, m)

EXAMPLE 5

(1) To a mixture of (2S,4R)-4-(4-chlorophenylsulfonylamino)-2 -[(Z)-5-methoxycarbonyl-1-pentenyl]pyrrolidine (356 mg) and nicotinaldehyde (98.6 mg) in methanol (5 ml) were added acetic acid (0.1 ml) and sodium cyanoborohydride (58 mg) and the mixture was stirred at room temperature for 3 hours. Saturated aqueous sodium bicarbonate (20 ml) was added to the solution and the aqueous solution was extracted with chloroform (50 ml). The organic layer was washed with brine and dried over magnesium sulfate. Re solvent was evaporated in vacuo and the residue was chromatographed on a silica gel (10 g) column with a mixture of chloroform and methanol (99:1) to give (2S,4R)-4-(4-chlorophenylsulfonylamino)-2-[(Z)-5 -methoxycarbonyl-1-pentenyl]-1-(3-pyridylmethyl)pyrrolidine (340 mg).

The following compounds were obtained according to a similar manner to that of Example 5(1).

(2) (2S,4R)-1-Benzyl-4-(4-chlorophenylsulfonylamino)-2 -[(Z)-5-methoxycarbonyl-1-pentenyl]pyrrolidine ¹H-NMR (CDCl₃) δ ppm: 1.5–2.0 (5H, m), 2.07 (2H, q, J=6.5 Hz), 2.31 (2H, t, J=6.5 Hz), 3.0–3.2 (2H, m), 3.33 (1H, q, J=8.5 Hz), 3.68 (3H, s), 3.63 (1H, m), 3.86 (1H, d, J=12.5 Hz), 4.96 (1H, d, J=8.5 Hz), 5.31 (1H, dd, J=9.5, 10.5 Hz), 5.53 (1H, dt, J=10.5, 7.5 Hz), 7.1–7.3 (5H, m), 7.44 (2H, d, J=8.5 Hz), 7.77 (2H, d, J=8.5 Hz)

(3) (2S,4R)-1-(4-Chlorophenylmethyl)-4-(4-chlorophenylsulfonylamino)- 2-[(Z)-5-methoxycarbonyl-1-pentenyl]pyrrolidine ¹H-NMR (CDCl₃) δ ppm: 1.6–2.0 (5H, m), 2.08 (2H, m), 2.28 (2H, t, J=7.0 Hz), 3.04 (2H, m), 3.32 (1H, q, J=7 Hz), 3.68 (1H, m), 3.69 (3H, s), 3.82 (1H, d, J=12.5 Hz), 4.83 (1H, d, J=7.5 Hz), 5.29 (1H, t, J=10 Hz), 5.50 (1H, dt, J=10, 8 Hz), 7.12 (2H, d, J=8 Hz), 7.32 (2H, d, J=8 Hz), 7.48 (2H, d, J=8.5 Hz), 7.79 (2H, d, J=8.5 Hz)

(4) (2S,4R)-4-(4-Chlorophenylsulfonylamino)-2-[(Z)-5 -methoxycarbonyl-1-pentenyl]-1-(4-methylphenylmethyl)pyrrolidine ¹H-NMR (CDCl₃) δ ppm: 1.6–1.8 (4H, m), 1.8–2.0 (2H, m), 2.0–2.2 (2H, m), 2.1–2.4 (3H, m), 2.34 (3H, s), 2.9–3.1 (2H, m), 3.29 (1H, q, J=9 Hz), 3.68 (3H, s), 3.10 (1H, m), 3.82 (1H, d, J=13 Hz), 4.85 (1H, m), 5.32 (1H, d, J=10 Hz), 5.52 (1H, dt, J=11, 7.5 Hz), 7.0–7.15 (4H, m), 7.54 (1H, d, J=9 Hz), 7.76 (2H, d, J=9 Hz)

(5) (2S,4R)-4-(4-Chlorophenylsulfonylamino)-2-[(Z)-5 -methoxycarbonyl-1-pentenyl]-1-(4-methoxyphenylmethyl)pyrrolidine ¹H-NMR (CDCl₃) δ ppm: 1.6–1.9 (5H, m), 2.05–2.15 (2H, m), 2 30 (2H, t, J=7.5 Hz) 3.00 (1H, d, J=13 Hz), 3.06 (1H, dd, J=10, 7.5 Hz), 3.29 (1H, q, J=9 Hz), 3.69 (3H, s), 3.7–3.85 (2H, m), 3.80 (3H, s), 4.84 (1H, d, J=7.5 Hz), 5.30 (1H, t, J=10 Hz), 5.52 (1H, dt, J=10, 7.5 Hz), 6.81 (2H, d, J=9 Hz), 7.09 (2H, d, J=9 Hz), 7.45 (2H, d, J=9 Hz), 7.77 (2H, d, J=9 Hz)

(6) (2S,4R)-4-(4-Chlorophenylsulfonylamino)-1-(3,4-dichlorophenylmethyl)-2-[(Z)-5-methoxycarbonyl-1-pentenyl]pyrrolidine $^1$H-NMR (CDCl$_3$) δ ppm: 1.6–2.0 (5H, m), 2.0–2.15 (2H, m), 2.30 (2H, t, J=7 Hz), 3.04 (1H, d, J=14 Hz), 3.09 (1H, dd, J=7.5, 10 Hz), 3.35 (1H, q, J=10 Hz), 3.67 (3H, s), 3.73 (1H, m), 3.80 (1H, d, J=14 Hz), 4.80 (1H, d, J=7.5 Hz), 5.27 (1H, d, J=11 Hz), 5.53 (1H, dt, J=11, 7.5 Hz), 7.02 (1H, dd, J=3, 10 Hz), 7.2–7.4 (2H, m), 7.47 (2H, d, J=9 Hz), 7.78 (2H, d, J=9 Hz)

(7) (2S,4R)-4-(4-Chlorophenylsulfonylamino)-2-[(Z)-5-methoxycarbonyl-1-pentenyl]-1-(4-phenylphenylmethyl)pyrrolidine $^1$H-NMR (CDCl$_3$) δ ppm: 1.6–1.8 (3H, m), 1.95 (1H, m), 2.08 (2H, m), 2.31 (1H, t, J=7.5 Hz), 3.11 (1H, d, J=14 Hz), 3.15 (1H, t, J=7 Hz), 3.36 (1H, q, J=7.5 Hz), 3.71 (1H, s), 3.85 (1H, m), 3.91 (1H, d, J=14 Hz), 4.80 (1H, d, J=7.5 Hz), 5.34 (1H, t, J=10 Hz), 5.55 (1H, dt, J=10, 7.5 Hz), 7.19 (2H, d, J=9 Hz), 7.3–7.65 (9H, m), 7.83 (2H, d, J=9 Hz)

(8) (2S,4R)-4-(4-Chlorophenylsulfonylamino)-1-(4-cyanophenylmethyl)-2-[(Z)-5-methoxycarbonyl-1-pentenyl]pyrrolidine $^1$H-NMR (CDCl$_3$) δ ppm: 1.55–1.80 (4H, m), 1.9–2.15 (3H, m), 2.30 (2H, t, J=7.5 Hz), 3.08 (1H, m), 3.15 (1H, d, J=14 Hz), 3.38 (1H, q, J=9 Hz), 3.69 (3H, s), 3.76 (1H, m), 3.92 (1H, d, J=14 Hz), 5.00 (1H, m), 5.25 (1H, dd, J=10, 11 Hz), 5.53 (1H, dt, J=10, 7.5 Hz), 7.32 (2H, d, J=9 Hz), 7.46 (2H, d, J=9 Hz), 7.59 (2H, d, J=9 Hz), 7.78 (2H, d, J=9 Hz)

(9) (2S,4R)-4-(4-Chlorophenylsulfonylamino)-1-(2-hydroxyphenylmethyl)-2-[(Z)-5-methoxycarbonyl-1-pentenyl]pyrrolidine $^1$H-NMR (CDCl$_3$) δ ppm: 1.6–1.75 (2H, m), 1.87 (2H, m), 2.05 (2H, t, J=7 Hz), 2.16 (1H, m), 2.28 (2H, t, J=7 Hz), 3.23 (1H, d, J=13 Hz), 3.25 (1H, dd, J=6, 11 Hz), 3.52 (1H, q, J=7.5 Hz), 3.72 (3H, s), 3.81 (1H, m), 4.17 (1H, d, J=13 Hz), 5.32 (1H, t, J=10 Hz), 5.61 (1H, dt, J=6, 7.5 Hz), 6.77 (2H, d, J=9 Hz), 6.91 (1H, d, J=7 Hz), 7.14 (1H, dt, J=7, 1 Hz), 7.47 (2H, d, J=9 Hz), 7.78 (2H, d, J=9 Hz)

(10) (2S,4R)-4-(4-Chlorophenylsulfonylamino)-2-[(Z)-5-methoxycarbonyl-1-pentenyl]-1-(2-thienylmethyl)pyrrolidine $^1$H-NMR (CDCl$_3$) δ ppm: 1.6–1.9 (4H, m), 2.05–2.15 (3H, m), 2.30 (2H, t, J=7.5 Hz), 3.19 (1H, dd, J=7.5, 10 Hz), 3.39 (1H, q, J=7.5 Hz), 3.47 (1H, d, J=15 Hz), 3.68 (3H, s), 3.80 (1H, m), 3.96 (1H, d, J=15 Hz), 4.82 (1H, broad s), 5.30 (1H, t, J=10 Hz), 5.54 (1H, dt, J=10, 7.5 Hz), 6.80 (1H, d, J=5 Hz), 6.92 (1H, dd, J=5, 3.5 Hz), 7.20 (1H, dd, J=1, 5 Hz), 7.56 (2H, d, J=9 Hz), 7.78 (2H, d, J=9 Hz)

(11) (2S,4R)-4-(4-Chlorophenylsulfonylamino)-1-(2-furylmethyl)-2-[(Z)-5-methoxycarbonyl-1-pentenyl]pyrrolidine $^1$H-NMR (CDCl$_3$) δ ppm: 1.6–1.95 (5H, m), 2.0–2.15 (2H, m), 2.30 (2H, t, J=7.5 Hz), 3.15–3.4 (3H, m), 3.68 (3H, s), 3.78 (1H, d, J=15 Hz), 3.81 (1H, m), 4.82 (1H, d, J=9 Hz), 5.27 (1H, t, J=10 Hz), 5.52 (1H, dt, J=10, 7.5 Hz), 6.11 (1H, s), 6.30 (1H, s), 7.34 (1H, s), 7.47 (2H, d, J=9 Hz), 7.78 (2H, d, J=9 Hz)

(12) (2S,4R)-4-(4-Chlorophenylsulfonylamino)-2-[(Z)-5-methoxycarbonyl-1-pentenyl]-1-(2-pyrazinylmethyl)pyrrolidine $^1$H-NMR (CDCl$_3$) δ ppm: 1.6–1.9 (4H, m), 2.05 (2H, m), 2.25 (1H, m), 2.28 (2H, t, J=6.5 Hz), 3.25 (1H, dd, J=10, 7.5 Hz), 3.51 (1H, d, J=14 Hz), 3.53 (1H, m), 3.68 (3H, s), 3.84 (1H, m), 4.02 (1H, d, J=14 Hz), 5.2–5.35 (2H, m), 5.52 (1H, dt, J=10, 7 Hz), 7.47 (2H, d, J=8.5 Hz), 7.78 (2H, d, J=8.5 Hz), 8.45–8.55 (3H, m)

(13) (2S,4R)-4-(4-Chlorophenylsulfonylamino)-1-hexyl-2-[-(Z)-5-methoxycarbonyl-1-pentenyl]pyrrolidine $^1$H-NMR (CDCl$_3$) δ ppm: 0.87 (3H, t, J=7 Hz), 1.2–1.4 (8H, m), 1.6–1.8 (4H, m), 1.9–2.1 (4H, m), 2.30 (2H, t, J=7 Hz), 2.59 (1H, dt, J=7, 13 Hz), 3.17 (1H, q, J=8 Hz), 3.36 (1H, dd, J=7.5, 10 Hz), 3.70 (3H, s), 3.80 (1H, m), 4.86 (1H, broad), 5.20 (1H, dd, J=10, 11 Hz), 5.47 (1H, dt, J=11, 7.5 Hz), 7.50 (2H, d, J=9 Hz), 7.81 (2H, d, J=9 Hz)

(14) (2S,4R)-4-(4-Chlorophenylsulfonylamino)-2-[(Z)-5-methoxycarbonyl-1-pentenyl]-1-(2-phenylethyl)pyrrolidine $^1$H-NMR (CDCl$_3$) δ ppm: 1.6–1.85 (4H, m), 2.0–2.1 (3H, m), 2.25–2.4 (3H, m), 2.6–2.75 (2H, m), 2.85 (1H, dd, J=10, 13 Hz), 3.38 (1H, q, J=8 Hz), 3.43 (1H, dd, J=10, 7.5 Hz), 3.65 (3H, s), 3.81 (1H, m), 4.95 (1H, d, J=7.5 Hz), 5.21 (1H, t, J=10 Hz), 5.48 (1H, dt, J=10, 7.5 Hz), 7.05–7.35 (5H, m), 7.50 (2H, d, J=9 Hz), 7.71 (2H, d, J=9 Hz)

(15) (2S,4R)-4-(4-Chlorophenylsulfonylamino)-2-[(Z)-5-methoxycarbonyl-1-pentenyl]-1-(3-phenylpropyl)pyrrolidine $^1$H-NMR (CDCl$_3$) δ ppm: 1.6–1.85 (6H, m), 1.95–2.1 (4H, m), 2.28 (2H, t, J=7.5 Hz), 2.5–2.7 (3H, m), 3.19 (1H, q, J=9 Hz), 3.37 (1H, J=10, 7.5 Hz), 3.68 (3H, s), 3.80 (1H, m), 5.20 (1H, t, J=10 Hz), 5.46 (1H, dd, J=7.5, 12 Hz), 7.1–7.3 (5H, m), 7.50 (2H, d, J=9 Hz), 7.80 (2H, d, J=9 Hz)

(16) (2S,4R)-4-(4-Chlorophenylsulfonylamino)-2-[(Z)-4-methoxycarbonyl-1-butenyl]-1-(3-pyridylmethyl)pyrrolidine $^1$H-NMR (CDCl$_3$) δ ppm: 1.7–1.9 (2H, m), 2.00 (1H, m), 2.3–2.4 (4H, m), 3.08 (1H, dd, J=6, 10 Hz), 3.13 (1H, d, J=14 Hz), 3.42 (1H, q, J=9 Hz), 3.66 (3H, s), 3.78 (1H, m), 3.35 (1H, d, J=14 Hz), 5.24 (1H, d, J=7.5 Hz), 5.28 (1H, t, J=10 Hz), 5.4–5.6 (1H, m), 7.22 (1H, dd, J=5, 7.5 Hz), 7.45 (2H, d, J=9 Hz), 7.56 (1H, m), 7.78 (2H, d, J=9 Hz), 8.4–8.6 (2H, m)

EXAMPLE 6

A solution of (2S,4R)-1-benzyl-4-(4-chlorophenyl-sulfonylamino)-2-[(Z)-5-methoxycarbonyl-1-pentenyl]pyrrolidine (320 mg) in a mixture of methanol (5 ml) and 1N-sodium hydroxide (3 ml) was stirred at room temperature for 3 hours and the volatile solvent was evaporated in vacuo. Water (20 ml) was added to the residue and the aqueous solution was adjusted to pH 7 with 1N-hydrochloric acid. The precipitated solid was collected by filtration and dried in vacuo to give (2S,4R)-1-benzyl-2-[(Z)-5-carboxy-1-pentenyl]-4-(4-chlorophenylsulfonylamino)pyrrolidine (176 mg).

mp: 87°–91° C.

$^1$H-NMR (CDCl$_3$) δ ppm: 1.71 (2H, m), 2.02 (2H, m), 2.17 (2H, m), 2.26 (2H, t, J=6.5 Hz), 2.46 (1H, dd, J=5, 11 Hz), 3.10 (1H, dd, J=6.5, 11 Hz), 3.65 (1H, d, J=12.5 Hz), 3.9–4.0 (2H, m), 4.11 (1H, m), 5.45 (1H, t, J=10 Hz), 5.73 (1H, dt, J=10, 7.5 Hz), 7.23 (5H, s), 7.38 (2H, d, J=8.5 Hz), 7.76 (2H, d, J=8.5 Hz)

EXAMPLE 7

The following compounds were obtained according to similar manners to those of Examples 2(1) and 6.

(1) (2S,4R)-2-[(Z)-5-Carboxy-1-pentenyl]-4-(4-chlorophenylsulfonylamino)-1-(2-quinolylmethyl)pyrrolidine ¹H-NMR (CDCl₃) δ ppm: 1.6–1.75 (2H, m), 2.05–2.2 (4H, m), 2.3–2.4 (2H, m), 2.92 (1H, m), 3.54 (1H, m), 4.03 (1H, m), 4.12 (1H, d, J=14 Hz), 4.40 (1H, d, J=14 Hz), 4.48 (1H, m), 5.5–5.7 (2H, m), 7.35 (2H, d, J=8.5 Hz), 7.5–7.85 (6H, m), 8.07 (1H, d, J=8.5 Hz), 8.18 (1H, d, J=8.5 Hz)

(2) (2S,4R)-1-(2-Benzoxazolylmethyl)-2-[(Z)-5-carboxy-1-pentenyl] 4-(4-chlorophenylsulfonylamino)pyrrolidine ¹H-NMR (CDCl₃) δ ppm: 1.55–1.7 (2H, m), 1.75–2.05 (4H, m), 2.26 (2H, t, J=7 Hz), 2.58 (1H, dd, J=2, 10 Hz), 3.44 (1H, dd, J=7, 10 Hz), 3.85–4.05 (2H, m), 3.97 (1H, d, J=16 Hz), 4.12 (1H, d, J=16 Hz), 5.28 (1H, t, J=10 Hz), 5.53 (1H, dt, J=10, 7 Hz), 7.3–7.45 (4H, m), 7.52 (1H, m), 7.78 (1H, d, J=8.5 Hz), 7.80 (1H, m)

(3) (2S,4R)-2-[(Z)-5-Carboxy-1-pentenyl]-4-(4-chlorophenylsulfonylamino)-1-(2-pyrazinylmethyl)pyrrolidine ¹H-NMR (CDCl₃) δ ppm: 1.66 (2H, m), 1.87 (2H, m), 2.10 (2H, m), 2.3–2.4 (3H, m), 3.21 (1H, m), 3.57 (1H, d, J=14 Hz), 3.68 (1H, m), 3.85 (1H, m), 4.02 (1H, d, J=14 Hz), 5.30 (1H, t, J=10 Hz), 5.54 (1H, dt, J=10, 7 Hz), 7.45 (2H, d, J=8.5 Hz), 7.78 (2H, d, J=8.5 Hz), 8.5–8.55 (2H, m), 8.58 (1H, m)

(4) (2S,4R)-2-[(Z)-4-Carboxy-1-butenyl]-4-(4-chlorophenylsulfonylamino)-1-(3-pyridylmethyl)pyrrolidine ¹H-NMR (CDCl₃) δ ppm: 1.85 (2H, m), 2.10 (2H, m), 2.3–2.5 (4H, m), 3.05 (1H, dd, J=10, 7 Hz), 3.28 (1H, d, J=13 Hz), 3.65 (1H, q, J=9 Hz), 3.70 (1H, m), 3.82 (1H, d, J=13 Hz), 5.30 (1H, t, J=10 Hz), 5.58 (1H, m), 7.27 (1H, m), 7.41 (2H, d, J=9 Hz), 7.53 (1H, d, J=7.5 Hz), 7.76 (2H, d, J=9 Hz), 8.35–8.5 (2H, m)

(5) (2S,4R)-2-[(Z)-5-Carboxy-1-pentenyl]-4-phenylsulfonylamino-1-(3-pyridylmethyl)pyrrolidine ¹H-NMR (CDCl₃) δ ppm: 1.54 (2H, m), 1.85 (2H, m), 2.14 (2H, m), 2.2–2.4 (3H, m), 3.12 (1H, dd, J=7, 9 Hz), 3.41 (1H, d, J=13.5 Hz), 3.68 (1H, m), 3.85 (1H, m), 3.96 (1H, d, J=13.5 Hz), 5.36 (1H, t, J=10 Hz), 5.60 (1H, dt, J=10, 7 Hz), 7.30 (1H, dd, J=5, 7 Hz), 7.4–7.55 (3H, m), 7.7–7.8 (3H, m), 8.4–8.5 (2H, m)

(6) (2S,4R)-2-[(Z)-5-Carboxy-1-pentenyl]-1-(4-chlorophenylmethyl)-4-(4-chlorophenylsulfonylamino)pyrrolidine mp: 84°–86° C.

¹H-NMR (CDCl₃) δ ppm: 1.69 (2H, m), 1.98 (2H, m), 2.15 (2H, m), 2.28 (2H, m), 2.43 (1H, dd, J=5, 11 Hz), 3.16 (1H, m), 3.57 (1H, d, J=12.5 Hz), 3.85–4.1 (3H, m), 5.43 (1H, t, J=10 Hz), 5.68 (1H, m), 7.15–7.25 (4H, m), 7.42 (2H, d, J=8.5 Hz), 7.77 (2H, d, J=8.5 Hz)

(7) (2S,4R)-2-[(Z)-5-Carboxy-1-pentenyl]-4-(4-chlorophenylsulfonylamino)-1-(4-methylphenylmethyl)pyrrolidine ¹H-NMR (CDCl₃) δ ppm: 1.6–1.8 (2H, m), 1.9–2.1 (2H, m), 2.1–2.4 (4H, m), 2.31 (3H, s), 2.43 (1H, dd, J=5, 11 Hz), 3.05 (1H, dd, J=7, 11 Hz), 3.64 (1H, d, J=13 Hz), 3.93 (1H, d, J=13 Hz), 3.95 (1H, m), 4.12 (1H, m), 5.45 (1H, t, J=10 Hz), 5.74 (1H, dt, J=10, 7.5 Hz), 7.08 (2H, d, J=7 Hz), 7.15 (2H, d, J=7 Hz), 7.40 (2H, d, J=9 Hz), 7.75 (2H, d, J=9 Hz)

(8) (2S,4R)-2-[(Z)-5-Carboxy-1-pentenyl]-4-(4-chlorophenylsulfonylamino)-1-(4-methoxyphenylmethyl)pyrrolidine ¹H-NMR (CDCl₃) δ ppm: 1.6–1.8 (2H, m), 2.00 (2H, m), 2.15–2.3 (4H, m), 2.45 (1H, dd, J=5, 12 Hz), 3.08 (1H, dd, J=7.5, 12 Hz), 3.59 (1H, d, J=13 Hz), 3.78 (3H, s), 3.82 (1H, d, J=13 Hz), 3.95 (1H, m), 4.06 (1H, q, J=7.5 Hz), 5.42 (1H, t, J=10 Hz), 5.72 (1H, dt, J=10, 7.5 Hz), 6.80 (2H, d, J=9 Hz), 7.16 (2H, d, J=9 Hz), 7.40 (2H, d, J=9 Hz), 7.77 (2H, d, J=9 Hz)

(9) (2S,4R)-2-[(Z)-5-Carboxy-1-pentenyl]-4-(4-chlorophenylsulfonylamino)-1-(3,4-dichlorophenylmethyl)pyrrolidine ¹H-NMR (CDCl₃) δ ppm: 1.6–1.75 (2H, m), 1.9–2.05 (2H, m), 2.1–2.25 (2H, m), 2.3–2.45 (3H, m), 3.17 (1H, m), 3.42 (1H, m), 3.75–4.0 (3H, m), 5.42 (1H, t, J=10 Hz), 5.67 (1H, dt, J=10, 7 Hz), 7.1–7.4 (3H, m), 7.46 (2H, d, J=9 Hz), 7.78 (2H, d, J=9 Hz)

(10) (2S,4R)-2-[(Z)-5-Carboxy-1-pentenyl]-4-(4-chlorophenylsulfonylamino)-1-(4-phenylphenylmethyl)pyrrolidine ¹H-NMR (CDCl₃) δ ppm: 1.55–1.8 (2H, m), 1.85–2.0 (2H, m), 2.15–2.3 (2H, m), 2.3–2.4 (3H, m), 3.11 (1H, dd, J=7.5, 12 Hz), 3.52 (1H, d, J=13 Hz), 3.8–4.0 (3H, m), 5.40 (1H, t, J=12 Hz), 5.69 (1H, dt, J=12, 7.5 Hz), 7.15 (2H, d, J=9 Hz), 7.35–7.6 (9H, m), 7.83 (2H, d, J=9 Hz)

(11) (2S,4R)-2-[(Z)-5-Carboxy-1-pentenyl]-4-(4-chlorophenylsulfonylamino)-1-(4-cyanophenylmethyl)pyrrolidine ¹H-NMR (CDCl₃) δ ppm: 1.67 (2H, m), 1.88 (2H, m), 2.0–2.4 (5H, m), 3.10 (1H, m), 3.36 (1H, d, J=14 Hz), 3.37 (1H, m), 3.70 (1H, m), 3.85 (1H, m), 3.95 (1H, d, J=14 Hz), 5.35 (1H, t, J=10 Hz), 5.62 (1H, dt, J=10, 7.5 Hz), 7.37 (2H, d, J=9 Hz), 7.43 (2H, d, J=9 Hz), 7.56 (2H, d, J=9 Hz), 7.78 (2H, d, J=9 Hz)

(12) (2S,4R)-2-[(Z)-5-Carboxy-1-pentenyl]-4-(4-chlorophenylsulfonylamino)-1-(2-hydroxyphenylmethyl)pyrrolidine ¹H-NMR (CDCl₃+CD₃OD) δ ppm: 1.6–1.75 (2H, m), 2.0–2.2 (4H, m), 2.33 (2H, t, J=6.5 Hz), 2.70 (1H, dd, J=5.5, 11 Hz), 3.41 (1H, dd, J=6.5, 11 Hz), 3.64 (1H, d, J=13 Hz), 3.85–4.05 (2H, m), 4.77 (1H, d, J=13 Hz), 5.47 (1H, t, J=10 Hz), 5.73 (1H, dt, J=10, 7.5 Hz), 6.81 (2H, d, J=7.5 Hz), 7.10 (1H, dd, J=7.5, 1 Hz), 7.21 (1H, td, J=1, 7.5 Hz), 7.48 (1H, d, J=9 Hz), 7.78 (1H, d, J=9 Hz)

(13) (2S,4R)-2-[(Z)-5-Carboxy-1-pentenyl]-4-(4-chlorophenylsulfonylamino)-1-(2-thienylmethyl)pyrrolidine ¹H-NMR (CDCl₃) δ ppm: 1.6–1.85 (2H, m), 1.9–2.05 (2H, m), 2.1–2.25 (2H, m), 2.34 (2H, t, J=7 Hz), 2.48 (1H, dd, J=5, 11 Hz), 3.21 (1H, dd, J=7.5, 11 Hz), 3.85 (1H, d, J=15 Hz), 3.85–3.95 (2H, m), 4.08 (1H, d, J=15 Hz), 5.44 (1H, t, J=10 Hz), 5.70 (1H, dt, J=10, 7.5 Hz), 6.93 (2H, m), 7.23 (1H, dd, J=2, 4 Hz), 7.42 (2H, d, J=9 Hz), 7.78 (2H, d, J=9 Hz)

(14) (2S,4R)-2-[(Z)-5-Carboxy-1-pentenyl]-4-(4-chlorophenylsulfonylamino)-1-(2-furylmethyl)pyrrolidine ¹H-NMR (CDCl₃) δ ppm: 1.6–1.75 (2H, m), 1.8–2.95 (2H, m), 2.1–2.2 (2H, m), 2.25–2.4 (3H, m), 3.20 (1H, dd, J=11, 7.5 Hz), 3.51 (1H, d, J=14 Hz), 3.6–4.0 (3H, m), 5.32 (1H, t, J=10 Hz), 5.65 (1H, dt, J=10, 7.5 Hz), 6.19 (1H, d, J=3 Hz), 6.30 (1H, dd, J=3, 1.5 Hz), 7.32 (1H, d, J=1.5 Hz), 7.43 (2H, d, J=9 Hz), 7.80 (2H, d, J=9 Hz)

(15) (2S,4R)-2-[(Z)-5-Carboxy-1-pentenyl]-4-(4-chlorophenylsulfonylamino)-1-hexylpyrrolidine ¹H-NMR (CDCl₃) δ ppm: 0.83 (3H, t, J=7 Hz), 1.15–1.35 (8H, m), 1.5–1.8 (4H, m), 2.05–2.3 (5H, m), 2.73 (1H, m), 3.06 (1H, dd, J=4, 13 Hz), 3.38 (1H, dd, J=7, 10 Hz), 4.09 (1H, m), 4.35 (1H, m), 5.40 (1H, t, J=10 Hz), 5.79 (1H, dt, J=10, 7.5 Hz), 7.49 (1H, d, J=9 Hz), 7.85 (1H, d, J=9 Hz)

(16) (2S,4R)-2-[(Z)-5-Carboxy-1-pentenyl]-4-(4-chlorophenylsulfonylamino)-1-(2-phenylethyl)pyrrolidine ¹H-NMR (CDCl₃) δ ppm: 1.55–1.8 (2H, m), 2.0–2.35 (5H, m), 2.48 (1H, m), 2.8–3.1 (4H, m), 3.3–3.6 (2H, m), 4.15 (1H, m), 4.37 (1H, m), 5.41 (1H, t, J=10 Hz), 5.72 (1H, dt, J=10, 7.5 Hz), 7.0–7.3 (5H, m ), 7.45 (2H, d, J=9 Hz), 7.81 (2H, d, J=9 Hz)

(17) (2S,4R)-2-[(Z)-5-Carboxy-1-pentenyl]-4-(4 -chlorophenylsulfonylamino)-1-(3-phenylpropyl)pyrrolidine $^1$H-NMR (CDCl$_3$) δ ppm: 1.5–1.8 (2H, m), 1.9–2.3 (7H, m), 2.55–2.65 (3H, m), 2.91 (2H, m), 3.18 (1H, d, J=13 Hz), 3.63 (1H, m), 4.08 (1H, m), 4.48 (1H, m), 5.51 (1H, t, J=10 Hz), 5.79 (1H, dt, J=10, 7.5 Hz), 7.05–7.3 (5H, m), 7.41 (2H, d, J=9 Hz), 7.81 (2H, d, J=9 Hz)

(18) (2S,4R)-1-(2-Benzothiazolylmethyl)-2-[(Z)-5 -carboxy-1-pentenyl]-4-(4-chlorophenylsulfonylamino)pyrrolidine

EXAMPLE 8

(2S,4R)-1-(2-Benzothiazolylmethyl)-2-[(Z)-5-carboxy-1-pentenyl]-4 -(4-chlorophenylsulfonylamino)pyrrolidine was dissolved in 1N-sodium hydroxide and the solution was applied to a column of Diaion HP 20. The column was washed with water and the elution was carried out with 70% aqueous methanol. The object fractions were collected and the volatile solvent was evaporated in vacuo. The resulting aqueous solution was lyophilized to give sodium salt of (2S,4R)-1-(2-benzothiazolylmethyl)-2-[(Z)-5 -carboxy-1-pentenyl]-4-(4-chlorophenylsulfonylamino)pyrrolidine.

$^1$H-NMR (D$_2$O) δ ppm: 1.45 (2H, m), 1.70 (2H, t, J=7 Hz), 1.9–2.1 (5H, m), 2.81 (1H, m), 3.4–3.6 (2H, m), 3.61 (1H, d, J=14 Hz), 4.00 (1H, d, J=14 Hz), 5.15 (1H, t, J=10 Hz), 5.42 (1H, dt, J=10, 7 Hz), 7.25 (2H, d, J=8.5 Hz), 7.25–7.45 (2H, m), 7.52 (2H, d, J=8.5 Hz), 7.81 (2H, d, J=8.5 Hz)

Preparation 16

The following compound was obtained according to a similar manner to that of Preparation 7.

(2S,4R)-4-Benzyloxycarbonylamino-1 -t-butoxycarbonyl-2-methoxycarbonylpyrrolidine $^1$H-NMR (CDCl$_3$) δ ppm: 1.40 (9H, s), 1.94 (2H, 3.32 (1H, m), 3.73 (3H, s), 3.78 (1H, m), 4.25–4.40 (2H, m), 5.03 (1H, m), 5.10 (2H, s), 7.33 (5H, m)

Preparation 17

The following compound was obtained according to a similar manner to that of Preparation 8.

(2S,4R)-4-Benzyloxycarbonylamino-1 -t-butoxycarbonyl-2-formylpyrrolidine

Preparation 18

The following compound was obtained according to a similar manner to that of Preparation 12.

(2S,4R)-4-Benzyloxycarbonylamino-1 -t-butoxycarbonyl-2-[(Z)-5-carboxy-1-pentenyl]pyrrolidine $^1$H-NMR (CDCl$_3$) δ ppm: 1.40 (9H, s), 1.60–1.96 (4H, m), 2.13 (2H, m), 2.34 (2H, m), 3.40 (1H, m), 3.62 (1H, m), 4.28 (1H, m), 4.60 (1H, m), 5.15 (3H, m), 5.38 (2H, m), 7.34 (5H, m)

Preparation 19

The following compounds were obtained according to a similar manner to that of Preparation 13.

(1) (2S,4R)-4-(4-Chlorophenylsulfonylamino)-2-[(Z)-6 -methoxycarbonyl-1-hexenyl]pyrrolidine (2) (2S,4R)-2-[(Z)-5-Methoxycarbonyl-1-pentenyl]-4-[4 -(trifluoromethyl)phenylsulfonylamino]pyrrolidine $^1$H-NMR (CDCl$_3$) δ ppm: 1.6–1.75 (3H, m), 1.85 (1H, ddd, J=3.5, 6.5, 10 Hz), 2.08 (2H, q, J=6.5 Hz), 2.31 (2H, t, J=6.5 Hz), 2.73 (1H, dd, J=4, 10 Hz), 3.24 (1H, dd, J=6, 11 Hz), 3.68 (3H, s), 3.89 (1H, m), 4.01 (1H, q, J=7.5 Hz), 5.25–5.5 (2H, m), 7.78 (2H, d, J=8 Hz), 8.02 (2H, d, J=8 Hz)

(3) (2S,4R)-4-Benzyloxycarbonylamino-2-[(Z)-5-methoxy-1-pentenyl]pyrrolidine

EXAMPLE 9

The following compounds were obtained according to a similar manner to that of Example 5(1).

(1) (2S,4R)-4-(4-Chlorophenylsulfonylamino)-2-[(Z)-5 -methoxycarbonyl-1-pentenyl]-1-(3-quinolylmethyl)pyrrolidine $^1$H-NMR (CDCl$_3$) δ ppm: 1.65–1.9 (4H, m), 2.0–2.2 (3H, m), 2.33 (2H, t, J=7 Hz), 3.15 (1H, dd, J=7, 10 Hz), 3.30 (1H, d, J=13.5 Hz), 3.43 (1H, q, J=9 Hz), 3.68 (3H, s), 3.77 (1H, m), 4.05 (1H, d, J=13.5 Hz), 4.91 (1H, d, J=7.5 Hz), 5.35 (1H, t, J=10 Hz), 5.58 (1H, dt, J=10, 7.5 Hz), 7.42 (2H, d, J=8.5 Hz), 7.55 (1H, m), 7.65–7.8 (4H, m), 7.96 (1H, m), 8.10 (1H, d, J=8 Hz), 8.81 (1H, d, J=1.5 Hz)

(2) (2S,4R)-4-(4-Chlorophenylsulfonylamino)-2-[(Z)-5 -methoxycarbonyl-1-pentenyl]-1-(1-naphthylmethyl)pyrrolidine $^1$H-NMR (CDCl$_3$) δ ppm: 1.6–2.0 (4H, m), 2.18 (2H, m), 2.33 (2H, t, J=7.5 Hz), 2.91 (1H, dd, J=6, 10 Hz), 3.30 (1H, d, J=12.5 Hz), 3.44 (1H, q, J=10 Hz), 3.68 (3H, s , 4.40 (1H, d, J=12.5 Hz), 4.95 (1H, br s), 5.46 (1H, dd, J=10, 9 Hz), 5.63 (1H, dt, J=10, 7.5 Hz), 7.1–7.9 (10H, m), 8.15 (1H, m)

(3) (2S,4R)-4-(4-Chlorophenylsulfonylamino)-2-[(Z)-5 -methoxycarbonyl-1-pentenyl]-1-(2-naphthylmethyl)pyrrolidine $^1$H-NMR (CDCl$_3$) δ ppm: 1.66–2.03 (4H, m), 2.10 (2H, q, J=7.5 Hz), 2.30 (2H, t, J=7.5 Hz), 3.08 (1H, dd, J=10, 7.5 Hz), 3.21 (1H, d, J=12.5 Hz), 3.39 (1H, q, J=7.5 Hz), 3.68 (3H, s), 3.75 (1H, m), 4.02 (1H, d, J=12.5 Hz), 4.92 (1H, br s), 5.36 (1H, dd, J=10, 11 Hz), 5.56 (1H, dt, J=11, 7.5 Hz), 7.3–7.5 (5H, m), 7.60 (1H, br s), 7.67–7.90 (5H, m)

(4) (2S,4R)-1-[(4-Acetylaminophenyl)methyl]-4-(4 -chlorophenylsulfonylamino)-2-[(Z)-5-methoxycarbonyl-1-pentenyl]pyrrolidine $^1$H-NMR (CDCl$_3$) δ ppm: 1.55–1.95 (4H, m), 2.08 (2H, m), 2.16 (3H, s), 2.30 (2H, t, J=7.5 Hz), 2.95–3.10 (2H, m), 3.30 (2H, q, J=7.5 Hz), 3.68 (3H, s), 3.75 (1H, m), 3.8 (1H, d, J=12 Hz), 5.30 (1H, m), 5.50 (1H, dt, J=10, 7.5 Hz), 7.10 (2H, d, J=9.5 Hz), 7.41 (2H, d, J=9.5 Hz), 7.45 (2H, d, J=10 Hz), 7.58 (1H, br s), 7.76 (2H, d, J=10 Hz)

(5) (2S,4R)-4-(4-Chlorophenylsulfonylamino)-1 -[(4-hydroxyphenyl)methyl]-2-[(Z)-5-methoxycarbonyl-1-pentenyl]pyrrolidine $^1$H-NMR (CDCl$_3$) δ ppm: 1.60–2.20 (8H, m), 2.30 (2H, t, J=7.5 Hz), 3.02 (1H, d, J=12 Hz), 3.09 (1H, dd, J=7.5, 10 Hz), 3.31 (1H, q, J=7.5 Hz), 3.69 (3H, s), 3.70 (1H, m), 3.80 (1H, d, J=12 Hz), 5.33 (1H, t, J=10 Hz), 5.54 (1H, dt, J=10, 7.5 Hz), 6.64 (2H. d, J=10 Hz), 7.00 (2H, d, J=10 Hz), 7.44 (2H, d, J=10 Hz), 7.75 (2H, d, J=10 Hz)

(6) (2S,4R)-4-(4-Chlorophenylsulfonylamino)-1-[{4 -(dimethylamino)phenyl}methyl]-2-[(Z)-5-methoxycarbonyl-1-pentenyl]pyrrolidine $^1$H-NMR (CDCl$_3$) δ ppm: 1.60–1.95 (4H, m), 2.10 (2H, q, J=7.5 Hz), 2.30 (2H, t, J=7.5 Hz), 2.95 (6H, s), 2.90–3.10 (2H, m), 3.27 (1H, q, J=7.5 Hz), 3.69 (3H, s), 3.72 (1H, m), 3.78 (1H, d, J=12 Hz), 4.80 (1H, br s), 5.32 (1H, t, J=10 Hz), 5.51 (1H, dt, J=10, 7.5 Hz), 6.60 (2H, d, J=10 Hz), 7.01 (2H, d, J=10 Hz), 7.45 (2H, d, J=10 Hz), 7.75 (2H, d, J=10 Hz)

(7) (2S,4R)-4-(4-Chlorophenylsulfonylamino)-2-[(Z)-5-methoxycarbonyl-1-pentenyl]-1-(2-pyrrolylmethyl)pyrrolidine $^1$H-NMR (CDCl$_3$) δ ppm : 1.60–1.85 (4H, m), 1.95–2.15 (2H, m), 2.30 (2H, t, J=7.5 Hz), 3.10 (1H, dd, J=7.0, 10 Hz), 3.20 (1H, d, J=12 Hz), 3.32 (1H, q, J=7.5 Hz), 3.69 (3H, s), 3.33 (1H, m), 3.78 (1H, d, J=12 Hz), 5.10 (1H, br s), 5.25 (1H, t, J=10 Hz), 5.50 (1H, dt, J=10, 7.0 Hz), 5.92 (1H, m), 6.09 (1H, dd, J=2.5, 5.0 Hz), 6.69 (1H, dd, J=3.0 5.0 Hz), 7.46 (2H, d, J=10 Hz), 7.78 (2H, d, J=10 Hz), 8.40 (1H, br s)

(8) (2S,4R)-1-[(2-Chlorophenyl)methyl]-4-(4-chlorophenylsulfonylamino)-2-[(Z)-5-methoxycarbonyl-1-pentenyl]pyrrolidine $^1$H-NMR (CDCl$_3$) δ ppm: 1.60–1.90 (4H, m), 2.10 (3H, m), 2.30 (2H, t, J=7.5 Hz), 3.12 (1H, dd, J=10, 7.5 Hz), 3.30 (1H, d, J=12 Hz), 3.43 (1H, q, J=7.5 Hz), 3.70 (3H, s), 3.80 (1H, m), 3.88 (1H, d, J=12 Hz), 4.80 (1H, br s), 5.33 (1H, t, J=10 Hz), 5.52 (1H, dt, J=10, 7.5 Hz), 7.13–7.37 (4H, m), 7.45 (2H, d, J=10 Hz), 7.76 (2H, d, J=10 Hz)

(9) (2S,4R)-4-(4-Chlorophenylsulfonylamino)-1-ethyl-2-[(Z)-5-methoxycarbonyl-1-pentenyl]pyrrolidine $^1$H-NMR (CDCl$_3$) δ ppm: 1.00 (3H, t, J=7.0 Hz), 1.56–1.85 (4H, m), 1.87–2.15 (4H, m), 2.30 (2H, t, J=7.5 Hz), 2.71 (1H, m), 3.20 (1H, m), 3.40 (1H, dd, J=7.5, 10 Hz), 3.69 (3H, s), 3.81 (1H, m), 5.20 (1H, t, J=10 Hz), 5.49 (1H, dt, J=10, 7.5 Hz), 7.50 (2H, d, J=10 Hz), 7.81 (2H, d, J=10 Hz)

(10) (2S,4R)-4-(4-Chlorophenylsulfonylamino)-1-dodecyl-2-[(Z)-5-methoxycarbonyl-1-pentenyl]pyrrolidine $^1$H-NMR (CDCl$_3$) δ ppm: 0.88 (3H, t, J=7.5 Hz), 1.15–1.40 (20H, m), 1.55–1.80 (4H, m), 1.85–2.15 (4H, m), 2.30 (2H, t, J=7.5 Hz), 2.60 (1H, dt, J=7.5, 13 Hz), 3.18 (1H, q, J=7.5 Hz), 3.37 (1H, dd, J=8.0, 10 Hz), 3.70 (3H, s), 3.80 (1H, m), 4.88 (1H, m), 5.20 (1H, t, J=10 Hz), 5.47 (1H, dt, J=10, 7.5 Hz), 7.50 (2H, d, J=10 Hz), 7.82 (2H, d, J=10 Hz)

(11) (2S,4R)-4-(4-Chlorophenylsulfonylamino)-2-[(Z)-5-methoxycarbonyl-1-pentenyl]-1-(5-phenylpentyl)pyrrolidine $^1$H-NMR (CDCl$_3$) δ ppm: 1.20–1.45 (4H, m), 1.50–1.80 (6H, m), 1.85–2.10 (4H, m), 2.29 (2H, t, J=7.5 Hz), 2.58 (1H, m), 2.58 (2H, t, J=8.0 Hz), 3.15 (1H, q, J=8.0 Hz), 3.36 (1H, dd, J=7.5, 10 Hz), 3.68 (3H, s), 3.80 (1H, br s), 4.97 (1H, br s), 5.18 (1H, t, J=10 Hz), 5.46 (1H, dt, J=10, 7.5 Hz), 7.10–7.35 (5H, m), 7.50 (2H, d, J=10 Hz), 7.82 (2H, d, J=10 Hz)

(12) (2S,4R)-4-(4-Chlorophenylsulfonylamino)-2-[(Z)-5-methoxycarbonyl-1-pentenyl]-1-(4-phenylbutyl)pyrrolidine $^1$H-NMR (CDCl$_3$) δ ppm: 1.30–1.80 (6H, m), 1.83–2.12 (4H, m), 2.28 (2H, t, J=7.5 Hz), 2.50–2.70 (4H, m), 3.16 (1H, q, J=7.5 Hz), 3.34 (1H, dd, J=7.5, 10 Hz), 3.67 (3H, s), 3.80 (1H, m), 4.98 (1H, m), 5.17 (1H, t, J=10 Hz), 5.46 (1H, dt, J=10, 7.5 Hz), 7.10–7.34 (5H, m), 7.49 (2H, d, J=10 Hz), 7.80 (2H, d, J=10 Hz)

(13) (2S,4R)-4-(4-Chlorophenylsulfonylamino)-2-[(Z)-5-methoxycarbonyl-1-pentenyl]-1-[2-(3-pyridyl)ethyl]pyrrolidine $^1$H-NMR (CDCl$_3$) δ ppm: 1.6–1.9 (4H, m), 2.0–2.2 (3H, m), 2.2–2.4 (3H, m), 2.68 (2H, t, J=6 Hz), 2.84 (1H, m), 3.29 (1H, q, J=8.5 Hz), 3.44 (1H, dd, J=6, 9.5 Hz), 3.63 (3H, s), 3.80 (1H, m), 5.05–5.20 (2H, m), 5.47 (1H, dt, J=7.5, 11 Hz), 7.17 (1H, dd, J=5, 7.5 Hz), 7.45 (1H, m), 7.48 (2H, d, J=8 Hz), 7.80 (2H, d, J=8 Hz), 8.42 (2H, m)

(14) (2S,4R)-4-(4-Chlorophenylsulfonylamino)-1-[2-(1-imidazolyl)ethyl]-2 -[(Z)-5-methoxycarbonyl-1-pentenyl]pyrrolidine $^1$H-NMR (CDCl$_3$) δ ppm: 1.6–1.8 (4H, m), 2.0–2.2 (3H, m), 2.29 (2H, t, J=6.5 Hz), 2.50 (1H, m), 2.94 (1H, m), 3.25–3.4 (2H, m), 3.68 (3H, s), 3.78 (1H, m), 3.94 (2H, t, J=6 Hz), 5.07 (1H, t, J=10 Hz), 5.47 (dt, J=10, 7.5 Hz), 5.68 (1H, br d, J=7 Hz), 6.88 (1H, s), 7.0 (1H, s), 7.49 (2H, d, J=8 Hz), 7.50 (1H, s), 7.78 (2H, d, J=8 Hz)

(15) (2S,4R)-4-(4-Chlorophenylsulfonylamino)-2-[(Z)-6-methoxycarbonyl-1-hexenyl]-1-(3-pyridylmethyl)pyrrolidine $^1$H-NMR (CDCl$_3$) δ ppm: 1.3–1.45 (2H, m), 1.55–1.7 (2H, m), 1.76 (1H, m), 1.85 (1H, m), 1.95–2.1 (3H, m), 2.33 (2H, t, J=7 Hz), 3.08 (1H, m), 3.11 (1H, d, J=13.5 Hz), 3.36 (1H, q, J=8.5 Hz), 3.65 (3H, s), 3.75 (1H, m), 3.88 (1H, d, J=13.5 Hz), 5.24 (1H, t, J=8 Hz), 5.54 (1H, dt, J=8, 11 Hz), 7.23 (1H, dd, J=4.5, 7.5 Hz), 7.46 (2H, d, J=8 Hz), 7.54 (1H, m), 7.78 (2H, d, J=8 Hz), 8.4–8.5 (2H, m)

(16) (2S,4R)-2-[(Z)-5-Methoxycarbonyl-1-pentenyl]-1-(3-pyridylmethyl)-4-[4-(trifluoromethyl)phenylsulfonylamino]-pyrrolidine $^1$H-NMR (CDCl$_3$) δ ppm: 1.65–1.90 (4H, m), 2.0–2.15 (3H, m), 2.32 (2H, t, J=6.5 Hz), 3.10 (1H, m), 3.13 (1H, d, J=13 Hz), 3.40 (1H, q, J=8 Hz), 3.69 (3H, s), 3.27 (1H, m), 3.38 (1H, d, J=13 Hz), 5.2–5.35 (2H, m), 5.55 (1H, dt, J=11, 7 Hz), 7.22 (1H, dd, J=4.5, 7.5 Hz), 7.53 (1H, d, J=7.5 Hz), 7.77 (2H, d, J=8 Hz), 7.98 (2H, d, J=8 Hz), 8.4–8.5 (2H, m)

(17) (2S,4R)-2-[(Z)-5-Methoxycarbonyl-1-pentenyl]-1-phenylmethyl-4-[4-(trifluoromethyl)phenylsulfonylamino]pyrrolidine $^1$H-NMR (CDCl$_3$) δ ppm: 1.65–1.80 (4H, m), 1.80–1.95 (2H, m), 2.00–2.15 (2H, m), 2.29 (2H, t, J=7.5 Hz), 3.05 (1H, d, J=12 Hz), 3.09 (1H, t, J=8.0 Hz), 3.30 (1H, m), 3.67 (3H, s), 3.75 (1H, m), 3.86 (1H, d, J=12 Hz), 5.00 (1H, m), 5.30 (1H, t, J=10 Hz), 5.53 (1H, dt, J=10, 7.5 Hz), 7.10–7.40 (8H, m), 7.73 (2H, d, J=9.0 Hz), 7.95 (2H, d, J=9.0 Hz)

(18) (2S,4R)-4-Benzyloxycarbonylamino-2-[(Z)-5-methoxycarbonyl-1-pentenyl]-1-(phenylmethyl)pyrrolidine $^1$H-NMR (CDCl$_3$) δ ppm: 1.60–1.80 (4H, m), 1.90–2.20 (4H, m), 2.33 (2H, t, J=8 Hz), 3.12 (1H, d, J=12.5 Hz), 3.30 (2H, m), 3.65 (3H, s), 3.94 (1H, d, J=12.5 Hz), 4.18 (1H, m), 4.85 (1H, m), 5.07 (2H, s), 5.30–5.60 (2H, m), 7.20–7.35 (5H, m)

(19) (2S,4R)-2-[(Z)-5-Carboxy-1-pentenyl]-4-(4-chlorophenylsulfonylamino)-1-(3-pyridylmethyl)pyrrolidine hydrochloride $^1$H-NMR (D$_2$O-DCl) δ ppm: 1.5–1.65 (2H, m), 1.95–2.15 (4H, m), 2.24 (2H, t, J=6.5 Hz), 3.18 (1H, dd, J=5.5, 12.5 Hz), 3.60 (1H, dd, J=7.5, 12.5 Hz), 4.02 (1H, m), 4.5–4.7 (2H, m), 5.33 (1H, t, J=10 Hz), 5.83 (1H, dt, J=10, 11.5 Hz), 7.51 (2H, d, J=8 Hz), 7.83 (2H, d, J=8 Hz), 8.08 (1H, dd, J=5.5, 8 Hz), 8.63 (1H, m), 8.82 (1H, d, J=5.5 Hz), 8.90 (1H, s)

EXAMPLE 10

The following compounds were obtained according to similar manners to those of Examples 2(1) and 6.

(1) (2S,4R)-2-[(Z)-5-Carboxy-1-pentenyl]-4-(4-chlorophenylsulfonylamino)-1-(3-quinolylmethyl)pyrrolidine $^1$H-NMR (CDCl$_3$) δ ppm: 1.6–1.8 (2H, m), 1.85–1.95 (2H, m), 2.15–2.25 (2H, m), 2.25–2.4 (3H, m), 3.16 (1H, dd, (2) (2S,4R)-2-[(Z)-5-Carboxy-1-pentenyl]-4-(4 -chlorophenylsulfonylamino)-1-(4-thiazolylmethyl)pyrrolidine ¹H-NMR (CDCl₃) δ ppm: 1.6–1.8 (2H, m), 1.95–2.05 (2H, m), 2.1–2.2 (2H, m), 2.25–2.35 (2H, m), 2.65 (2H, dd, J=4.5, 11 Hz), 3.34 (1H, dd, J=6, 11 Hz), 3.85–3.95 (2H, m), 4.05–4.15 (2H, m), 5.45 (1H, t, J=10 Hz) 5.68 (1H, dt, J=10, 7.5 Hz), 7.42 (1H, m) 7.43 (2H, d, J=8 Hz), 7.77 (2H, d, J=8 Hz), 8.80 (1H, d, J=1.5 Hz)

(3) (2S,4R)-2-[(Z)-5-Carboxy-1-pentenyl]-4-(4 -chlorophenylsulfonylamino)-1-(5-thiazolylmethyl)pyrrolidine ¹H-NMR (CDCl₃) δ ppm: 1.65–1.9 (4H, m), 2.1–2.25 (3H, m), 2.32 (2H, t, J=7 Hz), 3.19 (1H, dd, J=7, 9 Hz),, 3.55 (1H, q, J=9 Hz), 3.65 (2H, d, J=14 Hz), 3.81 (1H, m), 4.03 (1H, d, J=14 Hz), 5.29 (1H, t, J=10 Hz), 5.58 (1H, dt, J=10, 7.5 Hz), 7.45 (2H, d, J=8.5 Hz), 7.68 (1H, s), 7.77 (1H, s), 8.80 (1H, s)

(4) (2S,4R)-2-[(Z)-5-Carboxy-1-pentenyl]-4-(4 -chlorophenylsulfonylamino)-1-[2-(3-pyridyl) ethyl]pyrrolidine ¹H-NMR (CDCl₃) δ ppm: 1.55–1.75 (2H, m), 1.9–2.0 (2H, m), 2.05–2.2 (2H, m), 2.29 (2H, t, J=6 Hz), 2.6–2.7 (2H, m), 2.8–3.0 (3H, m), 3.50 (1H, m), 3.8–4.0 (2H, m), 5.31 (1H, t, J=10 Hz), 5.62 (1H, dt, J=7.5, 11 Hz), 7.03 (1H, m), 7.45 (2H, d, J=8 Hz), 7.55 (1H, m), 7.83 (2H, d, J=8 Hz), 8.44 (2H, m)

(5) (2S,4R)-2-[(Z)-5-Carboxy-1-pentenyl]-4-(4 -chlorophenylsulfonylamino)-1-[2-(1-imidazolyl)ethyl]pyrrolidine ¹H-NMR (CDCl₃+CD₃OD) δ ppm: 1.5–1.7 (4H, m), 2.0–2.15 (3H, m), 2.23 (2H, t, J=7 Hz), 2.50 (1H, m), 2.92 (1H, m), 3.2–3.4 (2H, m), 3.70 (1H, m), 3.95 (2H , t, J=6 Hz), 5.10 (1H, t, J=10 Hz), 5.45 (1H, dt, J=7.5, 10 Hz), 6.96 (2H, s), 7.45 (2H, d, J=8 Hz), 7.63 (1H, s), 7.77 (2H, d, J=8 Hz)

(6) (2S,4R)-2-[(Z)-6-Carboxy-1-hexenyl]-4-(4 -chlorophenylsulfonylamino)-1-(3-pyridylmethyl)pyrrolidine ¹H-NMR (CDCl₃+CD₃OD) δ ppm: 1.35–1.45 (2H, m), 1.6–1.65 (2H, m), 1.65–1.85 (2H, m), 2.0–2.15 (3H, m), 2.30 (2H, t, J=8 Hz), 3.04 (1H, dd, J=7.5, 10 Hz), 3.13 (1H, d, J=13.5 Hz), 3.37 (1H, q, J=7.5 Hz), 3.23 (1H, m), 3.90 (1H, d, J=13.5 Hz), 5.22 (1H, t, J=8 Hz), 5.58 (1H, dt, J=10.5, 8 Hz), 7.29 (1H, dd, J=4.5, 8 Hz), 7.46 (2H, d, J=8 Hz), 7.63 (1H, dt, J=7.5, 1.5 Hz), 7.77 (1H, d, J=8 Hz), 8.35–8.45 (2H, m)

(7) (2S,4R)-2-[(Z)-5-Carboxy-1-pentenyl]-1-(3 -pyridylmethyl)-4-[4-(trifluoromethyl)phenylsulfonylamino]pyrrolidine ¹H-NMR (CDCl₃) δ ppm: 1.6–1.7 (2H, m), 1.8–1.9 (2H, m), 2.1–2.25 (3H, m), 2.3–2.4 (2H, m), 3.10 (1H, dd, J=6.5, 10 Hz), 3.32 (1H, d, J=13 Hz), 3.62 (1H, q, J=8 Hz), 3.81 (1H, m), 3.92 (1H, d, J=13 Hz), 5.30 (1H, t, J=10 Hz), 5.59 (1H, dt, J=10, 7.5 Hz), 7.30 (1H, dd, J=5, 8 Hz), 7.65–7.75 (3H, m), 7.97 (2H, d, J=8 Hz), 8.45–8.55 (2H, m)

(8) (2S,4R)-2-[(Z)-5-Carboxy-1-pentenyl]-4-(4 -chlorophenylsulfonylamino)-1-(3-pyridylmethyl)pyrrolidine hydrochloride ¹H-NMR (D₂O-DCl) δ ppm: 1.5–1.65 (2H, m), 1.95–2.15 (4H, m), 2.24 (2H, t, J=6.5 Hz), 3.18 (1H, dd, J=5.5, 12.5 Hz), 3.60 (1H, dd, J=7.5, 12.5 Hz), 4.02 (1H, m), 4.5–4.7 (2H, m), 5.33 (1H, t, J=10 Hz), 5.83 (1H, dt, J=10, 11.5 Hz), 7.51 (2H, d, J=8 Hz), 7.83 (2H, d, J=8 Hz), 8.08 (1H, dd, J=5.5, 8 Hz), 8.63 (1H, m), 8.83 (1H, d, J=5.5 Hz), 8.90 (1H, s)

(9) (2S,4R)-2-[(Z)-5-Carboxy-1-pentenyl]-4-(4 -chlorophenylsulfonylamino)-1-(1- naphthylmethyl)pyrrolidine ¹H-NMR (CDCl₃) δ ppm: 1.68 (2H, m), 1.90 (2H, m), 2.15 (2H, m), 2.30 (2H, t, J=7 Hz), 2.96 (1H, dd, J=7.5, 10 Hz), 3.59 (1H, d, J=12.5 Hz), 3.75 (2H, m), 4.60 (1H, d, J=12.5 Hz), 5.49 (1H, t, J=10 Hz), 5.68 (1H, dt, J=10.6 Hz), 7.20–7.55 (6H, m), 7.60–7.90 (4H, m), 8.00–8.15 (1H, m)

(10) (2S,4R)-2-[(Z)-5-Carboxy-1-pentenyl]-4-(4 -chlorophenylsulfonylamino)-1-(2-naphthylmethyl)pyrrolidine ¹H-NMR (CDCl₃) δ ppm: 1.65 (2H, m), 1.90 (2H, m), 2.13 (2H, m), 2.28 (2H, m), 3.10 (1H, dd, J=9.0, 10 Hz), 3.56 (1H, d, J=13 Hz), 3.91 (1H, m), 4.00 (1H, d, J=13 Hz), 5.39 (1H, t, J=10 Hz), 5.64 (1H, dt, J=10, 8.0 Hz), 7.20–7.90 (11H, m)

(11) (2S,4R)-1-[(4-Acetylaminophenyl)methyl]-2-[(Z)-5 -carboxy-1-pentenyl]-4-(4-chlorophenylsulfonylamino)pyrrolidine ¹H-NMR (DMSO-d₆) δ ppm: 1.43–1.70 (4H, m), 1.75–2.10 (2H, m), 2.00 (3H, s), 2.19 (2H, t, J=7.5 Hz), 2.79 (1H, m), 2.96 (1H, d, J=12 Hz), 3.70 (1H, d, J=12 Hz), 5.22 (1H, m), 5.48 (1H, m), 7.04 (2H, d, J=10 Hz), 7.48 (2H, d, J=10 Hz), 7.63 (2H, d, J=9 Hz), 7.76 (2H, d, J=9 Hz), 7.98 (1H, br s)

(12) (2S,4R)-2-[(Z)-5-Carboxy-1-pentenyl]-4-(4 -chlorophenylsulfonylamino)-1-[(4-hydroxyphenyl)methyl]pyrrolidine ¹H-NMR (DMSO-d₆) δ ppm: 1.50–1.75 (4H, m), 2.09 (2H, m), 2.20 (2H, t, J=7.5 Hz), 2.86 (1H, br s), 5.26 (1H, m), 5.50 (1H, m), 6.67 (2H, d, J=9.0 Hz), 6.95 (2H, d, J=9.0 Hz), 7.60 (2H, d, J=10 Hz), 7.78 (2H, d, J=10 Hz), 7.95 (1H, br s), 9.22 (1H, br s)

(13) (2S,4R)-2-[(Z)-5-Carboxy-1-pentenyl]-4-(4 -chlorophenylsulfonylamino)-1-[{4-(dimethylamino)phenyl} methyl]pyrrolidine ¹H-NMR (DMSO-d₆) δ ppm: 1.45–1.77 (4H, m) 2.06 (2H m), 2.20 (2H, t, J=7.5 Hz), 2.88 (6H, s), 5.30 (1H, m), 5.53 (1H, m), 6.64 (2H, d, J=10 Hz), 6.97 (2H, m), 7.65 (2H, d, J=10 Hz), 7.79 (2H, d, J=10 Hz)

(14) (2S,4R)-2-[(Z)-5-Carboxy-1-pentenyl]-4-(4 -chlorophenylsulfonylamino)-1-(2-pyrrolylmethyl)pyrrolidine ¹H-NMR (DMSO-d₆) δ ppm: 1.37 (2H, m), 1.48 (2H, m), 1.86 (2H, m), 2.00 (2H, t, J=7.5 Hz), 2.70–3.75 (6H, m), 5.12 (1H, t, J=10 Hz), 5.35 (1H, dt, J=10, 7.5 Hz), 5.63 (1H, br s), 5.75 (1H, br s), 6.45 (1H, br s), 7.46 (2H, d, J=10 Hz), 7.60 (2H, d, J=10 Hz), 7.93 (1H, br s)

(15) (2S,4R)-2-[(Z)-5-Carboxy-1-pentenyl]-1-[(2 -chlorophenyl)methyl]-4-(4-chlorophenylsulfonylamino)pyrrolidine ¹H-NMR (CDCl₃) δ ppm: 1.70 (2H, m), 1.90 (2H, m), 2.16 (2H, m), 2.30 (2H, m), 3.11 (1H, m), 3.50 (1H, m), 3.85 (2H, m), 3.97 (1H, d, J=12 Hz), 4.78 (1H, s), 5.38 (1H, t, J=10 Hz), 5.62 (1H, dt, J=10, 8.0 Hz), 7.11–7.55 (6H, m), 7.76 (2H, d, J=10 Hz)

(16) (2S,4R)-2-[(Z)-5-Carboxy-1-pentenyl]-4-(4 -chlorophenylsulfonylamino)-1-(diphenylmethyl)pyrrolidine ¹H-NMR (CDCl₃) δ ppm: 1.4–1.55 (4H, m), 1.9–2.05 (2H, m), 2.1–2.2 (3H, m), 2.32 (1H, m) 2.90 (1H, m), 3.9–4.1 (2H, m), 4.73 (1H, s), 5.35–5.45 (2H, m), 7.2–7.4 (12H, m), 7.74 (2H, d, J=8 Hz)

(17) (2S,4R)-2-[(Z)-5-Carboxy-1-pentenyl]-4-(4 -chlorophenylsulfonylamino)-1-ethylpyrrolidine ¹H-NMR (DMSO-d₆) δ ppm: 1.05 (3H, m), 1.50 (4H, m), 2.00 (4H, m), 2.18 (2H, m), 5.2–5.7 (2H, m), 7.69 (2H, m), 7.85 (2H, m)

(18) (2S,4R)-2-[(Z)-5-Carboxy-1-pentenyl]-4-(4-chlorophenylsulfonylamino)-1-dodecylpyrrolidine ¹H-NMR (CDCl₃) δ ppm: 0.88 (3H, t, J=7.5 Hz), 1.14–1.36 (20H, m), 1.36–1.55 (2H, m), 1.55–1.74 (2H, m), 1.86–2.15 (4H, m), 2.20 (2H, m), 2.56 (1H, m), 2.85 (1H, m), 3.15 (1H, m), 4.03 (1H, m), 5.24 (1H, m), 5.68 (1H, m), 7.47 (2H, d, J=10 Hz), 7.85 (2H, d, J=10 Hz)

(19) (2S,4R)-2-[(Z)-5-Carboxy-1-pentenyl]-4-(4-chlorophenylsulfonylamino)-1-(5-phenylpentyl)pyrrolidine ¹H-NMR (CDCl₃) δ ppm: 1.10–1.40 (2H, m), 1.40–1.80 (6H, m), 1.95–2.30 (6H, m), 2.50 (2H, t, J=7.5 Hz), 2.90 (2H, m), 3.18 (1H, m), 3.70 (1H, m), 4.10 (1H, m), 4.50 (1H, m), 5.15 (1H, t, J=10 Hz), 5.81 (1H, dt, J=10, 7.0 Hz), 7.05–7.30 (5H, m), 7.45 (2H, d, J=10 Hz), 7.86 (2H, d, J=10 Hz)

(20) (2S,4R)-2-[(Z)-5-Carboxy-1-pentenyl]-4-(4-chlorophenylsulfonylamino)-1-(4-phenylbutyl)pyrrolidine ¹H-NMR (CDCl₃) δ ppm: 1.4–1.8 (6H, m), 2.08 (4H, m), 2.20 (2H, m), 2.55 (2H, m), 2.78 (2H, m), 3.05 (1H, m), 3.38 (1H, m), 4.05 (1H, m), 4.33 (1H, m), 5.40 (1H, t, J=10 Hz), 5.75 (1H, dt, J=10, 7.5 Hz), 7.00–7.34 (5H, m), 7.45 (2H, d, J=10 Hz), 7.84 (2H, d, J=10 Hz)

(21) (2S,4R)-2-[(Z)-5-Carboxy-1-pentenyl]-1-phenylmethyl-4-[4-(trifluoromethyl)phenylsulfonylamino]pyrrolidine ¹H-NMR (CDCl₃) δ ppm: 1.40–1.85 (2H, m), 2.10–2.40 (6H, m), 2.85 (1H, dd, J=5.0, 11 Hz), 3.10–3.45 (1H, m), 3.94 (1H, d, J=12 Hz), 4.05 (1H, m), 4.13 (1H, d, J=12 Hz), 4.48 (1H, q, J=7.5 Hz), 5.63 (1H, t, J=10 Hz), 5.82 (1H, d, J=10, 7.5 Hz), 7.20–7.40 (5H, m), 7.70 (2H, d, J=9.0 Hz), 7.96 (2H, d, J=9.0 Hz)

(22) (2S,4R)-2-[(Z)-5-Carboxy-1-pentenyl]-4-(4-methylphenylsulfonylamino)-1-(phenylmethyl)pyrrolidine ¹H-NMR (CDCl₃) δ ppm: 1.71 (2H, m), 2.07 (2H, m), 2.20 (2H, m), 2.34 (2H, t, J=7.5 Hz), 2.40 (3H, s), 2.64 (1H, dd, J=5.0, 11 Hz), 3.20 (1H, dd, J=7.5, 10 Hz), 3.78 (1H, d, J=12 Hz), 4.00 (1H, m), 4.04 (1H, d, J=12 Hz), 4.25 (1H, dt, J=7.5, 7.5 Hz), 5.57 (1H, t, J=10 Hz), 5.78 (1H, dt, J=10, 7.5 Hz), 7.20–7.40 (7H, m), 7.74 (2H, d, J=10 Hz)

(23) (2S,4R)-2-[(Z)-5-Carboxy-1-pentenyl]-4-(4-methoxyphenylsulfonylamino)-1-(phenylmethyl)pyrrolidine ¹H-NMR (CDCl₃) δ ppm: 1.69 (2H, m), 1.98 (2H, m), 2.17 (2H, m), 2.30 (2H, t, J=7.5 Hz), 2.50 (1H, dd, J=5.0, 10 Hz), 3.14 (1H, dd, J=7.5, 10 Hz), 3.61 (1H, d, J=12 Hz), 3.85 (3H, s), 4.00 (1H, d, J=12 Hz), 4.10 (2H, m), 5.49 (1H, t, J=10 Hz), 5.72 (1H, dt, J=10, 7.5 Hz), 6.91 (2H, d, J=9 Hz), 7.28 (5H, br s), 7.76 (2H, d, J=9 Hz)

EXAMPLE 11

The following compounds were obtained according to a similar manner to that of Example 1(1).

(1) (2S,4R)-4-(4-Chlorophenylsulfonylamino)-2-[(Z)-5-methoxycarbonyl-1-pentenyl]-1-(4-thiazolylmethyl)pyrrolidine ¹H-NMR (CDCl₃) δ ppm: 1.6–1.85 (4H, m), 2.02 (2H, q, J=7 Hz), 2.25 (1H, m), 2.28 (2H, t, J=7 Hz), 3.26 (1H, dd, J=6.5, 10 Hz), 3.52 (1H, q, J=7 Hz), 3.56 (1H, d, J=15 Hz), 3.67 (3H, s), 3.81 (1H, m), 3.99 (1H, d, J=15 Hz), 5.28 (1H, dd, J=9.5, 10 Hz), 5.45–5.6 (2H, m), 7.07 (1H, d, J=1.5 Hz), 7.46 (2H, d, J=8.5 Hz), 7.77 (2H, d, J=8.5 Hz), 8.81 (1H, d, J=1.5 Hz)

(2) (2S,4R)-4-(4-Chlorophenylsulfonylamino)-2-[(Z)-5-methoxycarbonyl-1-pentenyl]-1-(5-thiazolylmethyl)pyrrolidine ¹H-NMR (CDCl₃) δ ppm: 1.6–1.9 (4H, m), 2.05–2.15 (3H, m), 2.30 (2H, t, J=7 Hz), 3.18 (1H, dd, J=7, 10 Hz), 3.40 (1H, q, J=8 Hz), 3.54 (1H, d, J=14.5 Hz), 3.69 (3H, s), 3.78 (1H, m), 3.98 (1H, d, J=14.5 Hz), 5.07 (1H, d, J=7 Hz), 5.27 (1H, dd, J=10, 11 Hz), 5.53 (1H, dt, J=10, 7 Hz), 7.47 (2H, d, J=8.5 Hz), 7.63 (1H, s), 7.89 (2H, d, J=8.5 Hz), 8.72 (1H, s)

(3) (2S,4R)-4-(4-Chlorophenylsulfonylamino)-1-diphenylmethyl-2-[(Z)-5-methoxycarbonyl-1-pentenyl]pyrrolidine ¹H-NMR (CDCl₃) δ ppm: 1.4–1.5 (3H, m), 1.83 (1H, t, J=6 Hz), 2.0–2.15 (4H, m), 2.81 (1H, dd, J=6, 10 Hz), 3.64 (3H, s), 3.72 (1H, m), 3.89 (1H, m), 4.66 (1H, s), 4.78 (1H, d, J=8 Hz), 5.25–5.35 (2H, m), 7.15–7.3 (m, J=10 Hz), 7.40 (2H, d, J=8 Hz), 7.71 (2H, d, J=8 Hz)

EXAMPLE 12

A solution of (2S,4R)-1-[(4-acetylaminophenyl)methyl]-2-[(Z)-5-carboxy-1-pentenyl]-4-(4-chlorophenylsulfonylamino)pyrrolidine (200 mg) in 6N-hydrochloric acid (5 ml) was refluxed for 4 hours. The mixture was cooled in an ice bath and adjusted to pH 7 with 1N-sodium hydroxide. The precipitated solid was collected by filtration to give (2S,4R)-1-[(4-aminophenyl)methyl]-2-[(Z)-5-carboxy-1-pentenyl]-4-(4-chlorophenylsulfonylamino)pyrrolidine (95 mg).

¹H-NMR (DMSO-d₆) δ ppm: 1.45 (2H, m), 1.78 (2H, m), 1.97 (2H, m), 2.11 (2H, t, J=7.5 Hz), 2.54 (1H, br s), 3.05 (1H, br s), 3.30 (1H, br s), 3.65 (2H, br s), 3.84 (1H, d, J=12 Hz), 4.09 (1H, br s), 5.44 (1H, t, J=10 Hz), 5.61 (1H, dt, J=10, 7.5 Hz), 6.40 (2H, d, J=10 Hz), 6.86 (2H, d, J=10 Hz), 7.55 (2H, d, J=10 Hz), 7.71 (2H, d, J=10 Hz), 8.43 (1H, br s)

EXAMPLE 13

A solution of (2S,4R)-4-benzyloxycarbonylamino-2-[(Z)-5-methoxycarbonyl-1-pentenyl]-1-(phenylmethyl)pyrrolidine (700 mg) and 30% hydrogen bromide in acetic acid (2 ml) was stirred at room temperature for 2 hours and the solvent was evaporated in vacuo to give (2S,4R)-4-amino-2-[(Z)-5-methoxycarbonyl-1-pentenyl]-1-(phenylmethyl)pyrrolidine hydrobromide (800 mg) as an oil.

EXAMPLE 14

To a solution of (2S,4R)-4-amino-2-[(Z)-5-methoxycarbonyl-1-pentenyl]-1-(phenylmethyl)pyrrolidine hydrobromide (371 mg) in dichloromethane (4 ml) were added triethylamine (0.67 ml) and p-toluenesulfonyl chloride (200 mg) at 0° C. and the mixture was stirred at the same temperature for 1.5 hours. The solution was washed successively with water and brine and dried over magnesium sulfate. The solvent was evaporated in vacuo and the residue was chromatographed on a silica gel column with a mixture of ethyl acetate and n-hexane (1:2) as an eluent to give (2S,4R)-2-[(Z)-5-methoxycarbonyl-1-pentenyl]-4-(4-methylphenylsulfonylamino)-1-(phenylmethyl)pyrrolidine (249 mg) as an oil.

¹H-NMR (CDCl₃) δ ppm: 1.40–2.00 (4H, m), 2.09 (2H, m), 2.30 (2H, t, J=7.5 Hz), 2.41 (3H, s), 3.04 (1H, d, J=12 Hz), 3.08 (1H, t, J=8 Hz), 3.31 (1H, q, J=7.5 Hz), 3.70 (3H, s), 3.88 (1H, d, J=12 Hz), 4.78 (1H, d, J=8.0 Hz), 5.31 (1H, t, J=10 Hz), 5.50 (1H, dt, J=10, 7.5 Hz), 7.14–7.35 (7H, m), 7.70 (2H, d, J=10 Hz)

EXAMPLE 15

The following compounds were obtained according to a similar manner to that of Example 14.

(1) (2S,4R)-2-[(Z)-5-Methoxycarbonyl-1-pentenyl]-4-(4-methoxyphenylsulfonylamino)-1-(phenylmethyl)pyrrolidine $^1$H-NMR (CDCl$_3$) δ ppm: 1.60–1.95 (4H, m), 2.10 (2H, m), 2.30 (2H, t, J=7.5 Hz), 3.05 (1H, d, J=12 Hz), 3.07 (2H, m), 3.30 (1H, q, J=7.5 Hz), 3.69 (3H, s), 3.71 (1H, m), 3.86 (3H, s), 3.87 (1H, d, J=12 Hz), 4.72 (1H, d, J=9.0 Hz), 5.30 (1H, t, J=10 Hz), 5.50 (1H, dt, J=10, 7.5 Hz), 6.93 (2H, d, J=10 Hz), 7.11–7.33 (5H, m), 7.75 (2H, d, J=10 Hz)

(2) (2S,4R)-2-[(Z)-5-Carboxy-1-pentenyl]-4-(4-chlorophenylsulfonylamino)-1-(3-pyridylmethyl)pyrrolidine hydrochloride $^1$H-NMR (D$_2$O-DCl) δ ppm: 1.5–1.65 (2H, m), 1.95–2.15 (4H, m), 2.24 (2H, t, J=6.5 Hz), 3.18 (1H, dd, J=5.5, 12.5 Hz), 3.60 (1H, dd, J=7.5, 12.5 Hz), 4.02 (1H, m), 4.5–4.7 (2H, m), 5.33 (1H, t, J=10 Hz), 5.83 (1H, dt, J=10, 11.5 Hz), 7.51 (2H, d, J=8 Hz), 7.83 (2H, d, J=8 Hz), 8.08 (1H, dd, J=5.5, 8 Hz), 8.63 (1H, m), 8.82 (1H, d, J=5.5 Hz), 8.90 (1H, s)

What we claim is:

1. A compound of the formula:

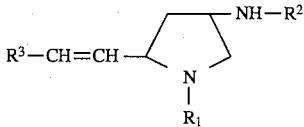

wherein $R^1$ is thienyl(lower)alkyl, furyl(lower)alkyl or pyrrolyl(lower)alkyl, $R^2$ is hydrogen or an acyl group, and $R^3$ is carboxyl(lower)alkyl, protected carboxyl(lower)alkyl, carboxyaryl or protected carboxyaryl, and a pharmaceutically acceptable salt thereof.

2. The compound of claim 1, wherein $R^2$ is hydrogen, phenyl(lower)alkoxycarbonyl, or phenylsulfonyl which may have 1 to 2 substituent(s) selected from the group consisting of halogen, lower alkyl, lower alkoxy and mono (or di or tri)halo(lower)alkyl, and $R^3$ is carboxy(lower)alkyl, esterified carboxy(lower)alkyl, carboxyphenyl or esterified carboxyphenyl.

3. The compound of claim 1, wherein $R^3$ is carboxy(lower)alkyl, lower alkoxycarbonyl(lower)alkyl, carboxyphenyl or lower alkoxycarbonylphenyl.

4. A pharmaceutical composition, which comprises:

as an active ingredient, a compound of claim 1 or a pharmaceutically acceptable salt thereof in admixture with a pharmaceutically acceptable carrier.

5. A method for treating thrombotic diseases, asthma, or nephritis, which comprises:

administering a compound of claim 1 or a pharmaceutically acceptable salt thereof too a human being or animals in need thereof.

* * * * *